(12) United States Patent
Ozaki et al.

(10) Patent No.: US 7,755,797 B2
(45) Date of Patent: *Jul. 13, 2010

(54) PICTURE COLOR TONE CONTROLLING METHOD AND APPARATUS

(75) Inventors: Ikuo Ozaki, Hiroshima (JP); Syuuichi Takemoto, Mihara (JP); Norifumi Tasaka, Mihara (JP)

(73) Assignee: Mitsubishi Heavy Industries, Ltd., Tokyo (JP)

(*) Notice: Subject to any disclaimer, the term of this patent is extended or adjusted under 35 U.S.C. 154(b) by 508 days.

This patent is subject to a terminal disclaimer.

(21) Appl. No.: 11/666,683

(22) PCT Filed: Nov. 14, 2005

(86) PCT No.: PCT/JP2005/020848

§ 371 (c)(1),
(2), (4) Date: Jun. 11, 2007

(87) PCT Pub. No.: WO2006/054521

PCT Pub. Date: May 26, 2006

(65) Prior Publication Data

US 2008/0216695 A1    Sep. 11, 2008

(30) Foreign Application Priority Data

Nov. 19, 2004 (JP) .............................. 2004-336507

(51) Int. Cl.
G06F 15/00 (2006.01)
H04N 1/46 (2006.01)
G06K 15/00 (2006.01)
G06K 9/00 (2006.01)
G06K 9/40 (2006.01)

(52) U.S. Cl. .................. 358/1.9; 358/504; 358/534; 358/3.06; 382/112; 382/162; 382/167; 382/266

(58) Field of Classification Search ............... 358/1.9, 358/500, 512, 504, 502, 534, 524, 538, 1.2, 358/3.01, 3.06, 3.27; 382/112, 266, 162, 382/167; 347/19, 43, 14; 400/61, 70, 76; 101/484, 365, 211
See application file for complete search history.

(56) References Cited

U.S. PATENT DOCUMENTS 6,389,968 B1 * 5/2002 Sugimoto et al. ........... 101/365
(Continued)

FOREIGN PATENT DOCUMENTS

JP    2001-18364    1/2001
(Continued)

OTHER PUBLICATIONS

New Edition; Color Science Handbook Second Version; by the Color Science Association of Japan; University of Tokyo Press.

*Primary Examiner*—Charlotte M Baker
(74) *Attorney, Agent, or Firm*—Manabu Kanesaka; Kenneth Berner; Benjamin Hauptman

(57) ABSTRACT

In a picture color tone control method and apparatus for a printing press, in order to make it possible to use an IRGB densitometer to perform color tone control even when printing is performed with a density which exceeds an estimated maximum color space, a target color mixture halftone density for each ink supplying unit width when a printing picture is divided with an ink supplying unit width of ink supplying apparatus 6, 7 is set, and an actual color mixture halftone density for each ink supplying unit width of an actually printed sheet obtained by printing is measured using an IRGB densitometer 1. The color mixture halftone densities are individually converted into tone values. Thereupon, for the conversion into actual tone values, the publicly known Neugebauer expression wherein the Yule-Nielsen coefficient n is set to such a value that the tone values and the color mixture halftone density value have a substantially linear relationship to each other is used. Further, the tone values are converted into a monochromatic halftone density, and a solid density difference corresponding to the difference between the target monochromatic halftone density and an actual monochromatic halftone density is determined using the Yule-Nielsen expression or the like. Then, the ink supplying amount is adjusted for each ink supplying unit width in response to the solid density difference.

14 Claims, 8 Drawing Sheets

U.S. PATENT DOCUMENTS 6,722,281 B2 * 4/2004 Yamamoto ................... 101/484
7,245,397 B2 * 7/2007 Yoshida ....................... 358/1.9

FOREIGN PATENT DOCUMENTS

| JP | 2001-47605 | 2/2001 |
| JP | 2001-277473 | 10/2001 |
| JP | 2004-106523 | 4/2004 |
| WO | WO 03/039134 | 5/2003 |

* cited by examiner

PICTURE COLOR TONE CONTROLLING METHOD AND APPARATUS

TECHNICAL FIELD

This invention relates to a picture color tone controlling method and apparatus for a printing press, and more particularly to a picture color tone controlling method and apparatus for controlling the color tone using an IRGB densitometer.

BACKGROUND ART

Various techniques have been proposed as a technique for color tone control of a picture of a printing press.

For example, in techniques disclosed in Patent Document 1 and Patent Document 2, color tone control is performed in such a procedure as described below.

First, a spectral reflectance of a picture printed by printing units of different colors is measured by a spectrometer. Then, the spectral reflectance (average spectral reflectance in an overall key zone) is arithmetically operated for each of key zones of ink keys, and the spectral reflectance of each key zone is converted into a color coordinate value (L*a*b*) proposed by the International Commission on Illumination. If the ink supplying amount for each color is adjusted and test printing is performed and then a printing sheet (hereinafter referred to as OK sheet) having a desired color tone is obtained, then the color coordinate value for each key zone of the OK sheet is set as a target color coordinate value. Then, actual printing is started, and the difference (color difference) between the color coordinate values of the OK sheet and a printing sheet (printing sheet obtained by actual printing is hereinafter referred to as actual printing sheet) is calculated for each of the key zones. Thereafter, an increasing and decreasing amount for the opening of the ink key of each printing unit with respect to the color difference is calculated, and the opening of each ink key of each printing unit is adjusted by online control so that the color difference may be reduced to zero.

However, according to the techniques disclosed in Patent Documents 1 and 2, a spectrometer is used as a measurement section. The spectrometer requires a high cost. Further, where an object of measurement (in this instance, a printing sheet) moves at a very high speed as in the case of a rotary press for newspapers, the spectrometer cannot follow up the measurement object because of the processing capacity thereof. Further, in the method described above, since the color tone control is started after an OK sheet is printed, a great amount of paper loss appears after the printing process is started until the OK sheet is printed. Further, in the method described above, a picture in the key zone of each ink key is averaged over the entire key zone and the color tone control is performed based on the spectral reflectance after the averaging. Therefore, where the image area ratio of the picture in a key zone is low, a measurement error of the spectrometer increases and the control is likely to be rendered instable. Further, particularly severe color tone management is sometimes requested regarding a specific noticed point in a picture depending upon an order from a customer. Where the color tone control is to be performed for a specific noticed point in such a manner as just described, data such as CIP4 data [JDF (Job Definition Format) data of the CIP4 (International Cooperation for Integration of Prepress, Press, and Postpress) standard] must be received as image data to be used as a reference from an upstream plate making step and color separation must be performed for a control point so that the ink supplying amount is estimated.

Thus, Patent Document 3 discloses a technique wherein, in order to solve such subjects as described above, color tone control is performed in accordance with the following procedure.

First, a target color mixture halftone density for each ink supplying unit width when a printing picture is divided by the ink supplying unit width of an ink supplying apparatus is set. It is to be noted that, where the ink supplying apparatus is an ink key apparatus, the ink supplying unit width of the ink supplying apparatus is the key width (key zone) of each ink key, but where the ink supplying apparatus is a digital pump apparatus, the ink supplying unit width is the pump width of each digital pump. It is to be noted that a setting method for the target color mixture halftone density is hereinafter described.

If printing is started and an actual printing sheet is obtained, then an actual color mixture halftone density for each ink supplying unit width of the actual printing sheet is measured using an IRGB densitometer. Then, actual tone values for each ink color corresponding to the actual color mixture halftone density are determined based on a corresponding relationship set in advance between tone values and color mixture halftone densities for the individual ink colors. As a method for determining actual tone values from an actual color mixture halftone density, a database wherein a relationship between tone values and color mixture halftone densities for individual ink colors is stored, for example, a database wherein data obtained by printing a color scale of the Japan Color (ISO12642) for Newspaper Printing established by the ISO/TC130 National Commission and actually measuring the color scale by means of an IRGB densitometer are stored, may be used. More simply, the database can be utilized also to utilize an approximate value calculated using the known Neugebauer expression. Further, target tone values for each ink color corresponding to the target color mixture halftone density are determined based on the corresponding relationship described above between tone values and color mixture halftone densities. Different from the actual tone values, the target tone values need not be determined every time, but it is sufficient to determine the target tone values once unless the target color mixture halftone density varies. For example, the target tone values may be determined at a point of time when the target color mixture halftone density is set.

Then, an actual monochromatic halftone density corresponding to the actual tone values is determined based on a corresponding relationship set in advance between tone values and monochromatic halftone densities. As a method of determining an actual monochromatic halftone density from actual tone values, a map or a table which represents a relationship between monochromatic halftone densities and tone values may be prepared such that the actual tone values are applied to the map or the table. More simply, the relationship described above may be approximated using the known Yule-Nielsen expression to determine the actual monochromatic halftone density. Meanwhile, a target monochromatic halftone density corresponding to the target tone values is determined based on the corresponding relationship described above between tone values and monochromatic halftone densities. Different from the actual monochromatic halftone density, the target monochromatic halftone density need not be determined every time, and it is sufficient to determine the target monochromatic halftone density once unless the target tone values vary. For example, the target monochromatic halftone density may be determined at a point of time when the target tone values are set.

Then, a solid density difference corresponding to a difference between the target monochromatic halftone density and the actual monochromatic halftone density under the target tone values is determined based on a corresponding relationship set in advance among tone values, monochromatic halftone densities and solid densities. As a method of determining the solid density difference, a map or a table which represents the corresponding relationship described above is prepared, and then the target tone values, target monochromatic halftone density and actual monochromatic halftone density are applied to the map or table. More simply, the relationship described above may be approximated using the known Yule-Nielsen expression to determine the solid density difference. Then, the ink supplying amount is adjusted for each of the ink supplying unit widths based on the determined solid density difference and the ink supplying amount for each color is controlled for each of the ink supplying unit widths. The adjustment amount of the ink supplying amount based on the solid density difference can be determined simply using the known API (Auto Preset Inking) function.

According to such a picture color tone controlling method as described above, since color tone control can be performed using not a spectrometer but an IRGB densitometer, the cost required for the measuring system can be reduced, and besides the picture color tone controlling method can be applied sufficiently also to a high speed printing press such as a rotary press for newspapers.

Meanwhile, as a technique for setting a target color mixture halftone density where kcmy tone values data of a printing object picture (for example, image data for plate making or the like) can be acquired from the outside (for example, a printing requesting source or the like), the following technique has been proposed.

First, the acquired image data (kcmy tone values data) are used to set a noticed pixel (the noticed pixel may be a single pixel or a plurality of contiguous pixels in a mass) corresponding to each of ink colors for each ink supplying unit width from among pixels which form the printing object picture. Then, the tone values of the noticed pixel are converted into a color mixture halftone density based on a corresponding relationship set in advance between tone values and color mixture halftone densities. Then, the color mixture halftone density of the noticed pixel is set as a target color mixture halftone density, and the actual color mixture halftone density of the set noticed pixel is measured.

According to the proposed technique, since color development can be estimated in a unit of a pixel by utilizing the database of Japan Color (ISO12642) or the like, color tone control can be performed for a particular noticed point (noticed pixel) of the picture at a point of time immediately after printing is started without waiting that an OK sheet is printed. It is to be noted that the kcmy tone values data may be bitmap data of the printing object picture (for example, data for 1 bit-Tiff plating making). Or, low resolution data corresponding to CIP4 data obtained by conversion of such bitmap data may be used alternatively.

It is to be noted that, as a setting method of a noticed point (noticed picture), a method is available wherein an image of a printing picture is displayed on a display apparatus such as a touch panel using bitmap data such that an operator may designate a noticed point arbitrarily. Also a method has been proposed wherein a pixel having a maximum density sensitivity, or a pixel having a maximum autocorrelation to the tone values, is automatically extracted for each ink color through arithmetic operation and is set as a noticed pixel. In a particular setting method of a noticed pixel, an autocorrelation sensitivity H is introduced such that a pixel having a maximum autocorrelation sensitivity H is determined as a pixel having a maximum autocorrelation and is set as a noticed pixel. For example, the autocorrelation sensitivity Hc to cyan can be represented, using pixel area ratio data (c, m, y, k), as "$Hc=c^p/(c+m+y+k)$" and a pixel having a maximum value of the autocorrelation sensitivity Hc is set as a noticed point of cyan. It is to be noted that p is an exponentiation of the autocorrelation.

If a pixel having a maximum autocorrelation with regard to tone values is extracted through arithmetic operation and set as a noticed pixel for each ink color and a target monochromatic halftone density and an actual monochromatic halftone density are calculated with regard to the noticed pixel and then the ink supplying amount is feedback controlled so that the actual monochromatic halftone density may approach the target monochromatic halftone density in such a manner as described above, then stabilized color tone control can be achieved.

Patent Document 1: Japanese Patent Laid-Open No. 2001-18364

Patent Document 2: Japanese Patent Laid-Open No. 2001-47605

Patent Document 3: Japanese Patent Laid-Open No. 2004-106523

DISCLOSURE OF THE INVENTION

Subject to be Solved by the Invention

Incidentally, according to the technique of Patent Document 3 described above, when it is tried to set a target color mixture halftone density or when it is tried to arithmetically operate tone values at present, a corresponding relationship between the tone valves and the color mixture halftone density is required. This corresponding relationship is produced as a conversion table or the known Neugebauer expression by printing a color scale of a certain reference density (although this reference density is prescribed to some degree by the Japan Color (ISO12642), it sometimes differs among different newspaper company).

In particular, a corresponding relationship between the tone values and the color mixture halftone density is set for a color space lower than a reference density which is provided by a maximum density of ink which is estimated upon printing. In general printing other than solid printing, the maximum density is not set to such a high level as a maximum density which can be printed, or in other words, the tone values are set to some fraction of the maximum density which can be printed and does not exceed 100%. Also the corresponding relationship between the tone values and the color mixture halftone density can be set, by setting the maximum density upon actual printing as a reference density, with a higher degree of accuracy than where the maximum density which can be printed is set as a value higher than the reference density. On the contrary, if the accuracy is substantially equal, then when a conversion table is produced or in a like case, since the object range is smaller, the production is facilitated as much.

However, if a color is measured which deviates from a color space of the conversion table or the known Neugebauer expression produced with the reference density, then monochromatic tone values conversion becomes impossible and disables control. In particular, upon actual printing, an operator sometimes prints with a density higher than an estimated maximum density (reference density) in accordance with a demand of a customer or the like. In this instance, as seen in FIG. 12, the density of ink deviates from a set color space, and it becomes impossible to use the set corresponding relationship between the tone values and the color mixture halftone density to perform conversion into the monochromatic tone values and also to perform color tone control.

The present invention has been made in view of such subjects as described above, and it is an object of the present invention to provide a picture color tone controlling method and apparatus for a printing press wherein, also where printing is performed with a density which exceeds an estimated maximum density, a set color space can be expanded readily to perform color tone control using an IRGB densitometer.

Means for Solving the Subject

In order to achieve the object described above, according to a picture color tone controlling method for a printing press of the present invention, a noticed pixel region to be noticed as an object of picture color tone control in a printing picture is selected (noticed pixel region selection step).

Then, a target color mixture halftone density is set regarding the noticed pixel region selected at the noticed pixel region selection step (target color mixture halftone density setting step). Then, actual printing is carried out, and an actual color mixture halftone density for each noticed pixel region on an actually printed sheet obtained by printing is measured using an IRGB densitometer (actual color mixture halftone density measurement step).

Thereafter, target tone values of each ink color corresponding to the target color mixture halftone density are calculated based on a corresponding relationship between tone values and color mixture halftone densities set in advance (target tone values calculation step). Together with this, actual tone values for each ink color corresponding to the actual color mixture halftone density are calculated based on the corresponding relationship between the tone values and the color mixture halftone densities (actual tone values calculation step).

Thereafter, a target monochromatic halftone density corresponding to the target tone values is calculated based on a corresponding relationship between tone values and monochromatic halftone densities set in advance (target monochromatic halftone density calculation step), and an actual monochromatic halftone density corresponding to the actual tone values is calculated based on the corresponding relationship between the tone values and the monochromatic halftone densities (actual monochromatic halftone density calculation step).

Thereafter, a solid density difference corresponding to a difference between the target monochromatic halftone density and the actual monochromatic halftone density under the target tone values is calculated based on a corresponding relationship among tone values, monochromatic halftone densities and solid densities set in advance (solid density difference calculation step), and an ink supplying amount is adjusted for each ink supplying unit width of an ink supplying apparatus based on the solid density difference (ink supplying amount adjustment step).

Particularly, in the picture color tone controlling method for a printing press of the present invention, at the target tone values calculation step and the actual tone values calculation step, as the corresponding relationship between the tone values and the color mixture halftone densities, solid density values $Di(\lambda)$ for wavelengths $\lambda$ of colors of I (infrared light), R (Red), G (Green), and B (Blue) are acquired in advance and a publicly known extended Neugebauer expression (A) is produced in advance wherein a Yule-Nielsen coefficient n is set to such a value that the tone values and the color mixture halftone density value have a substantially linear relationship to each other, and the target tone values and the actual tone values are determined using the publicly known extended Neugebauer expression (A):

[Expression 1]

$$10^{-Da(\lambda)/n} = (1-K)(1-c)(1-m)(1-y) + k(1-c)(1-m)(1-y)10^{-Dk(\lambda)/n} + c(1-k)(1-m)(1-y)10^{-Dc(\lambda)/n} + m(1-k)(1-c)(1-y)10^{-Dm(\lambda)/n} + y(1-k)(1-c)(1-m)10^{-Dy(\lambda)/n} + kc(1-m)(1-y)10^{-Dkc(\lambda)/n} + km(1-c)(1-y)10^{-Dkm(\lambda)/n} + ky(1-c)(1-m)10^{-Dky(\lambda)/n} + cm(1-k)(1-y)10^{-Dcm(\lambda)/n} + cy(1-k)(1-m)10^{-Dcy(\lambda)/n} + my(1-k)(1-c)10^{-Dmy(\lambda)/n} + kcm(1-y)10^{-Dkcm(\lambda)/n} + kcy(1-m)10^{-Dkcy(\lambda)/n} + kmy(1-c)10^{-Dkmy(\lambda)/n} + cmy(1-k)10^{-Dcmy(\lambda)/n} + kcmy10^{-Dkcmy(\lambda)/n} \quad (A)$$

where $Da(\lambda)$: color mixture halftone density value, k, c, m, y: tone values of corresponding inks, $Di(\lambda)$: solid density value of wavelength $\lambda$ of each color i (extracted from color scale data), I: one of Cyan, Magenta, Yellow, Black and color mixture of them, for example, Dc: solid density value of Cyan, Dm: solid density value of Magenta, Dy: solid density value of Yellow, Dk: solid density value of Black, Dcm: two-color overlapping solid density value of Cyan and Magenta, Dcy: two-color overlapping solid density value of Cyan and Yellow, Dmy: two-color overlapping solid density value of Magenta and Yellow, Dkc: two-color overlapping solid density value of Cyan and Black, Dkm: two-color overlapping solid density value of Magenta and Black Dky: two-color overlapping solid density value of Yellow and Black, Dcmy: three-color overlapping solid density value of Cyan, Magenta and Yellow, Dkcm: three-color overlapping solid density value of Cyan, Magenta and Black, Dkcy: three-color overlapping solid density value of Cyan, Yellow and Black, Dkmy: three-color overlapping solid density value of Magenta, Yellow and Black, Dcmyk: four-color overlapping solid density value of Cyan, Magenta, Yellow and Black $\lambda$: wavelength region of each of R, G, B, I, for example, R=650 nm, G=550 nm, B=450 nm, I=800 nm, and n: coefficient of Yule-Nielsen.

Preferably, the solid density value $Di(\lambda)$ for each of the wavelengths $\lambda$ of the colors of I (infrared light), R (Red), G (Green) and B (Blue) in the publicly known extended Neugebauer expression (A) is acquired from data obtained in advance by printing a color scale of the Japan Color (ISO12642) or the like under the standard density. In particular, by printing a color scale of the Japan Color (ISO12642) or the like with a reference density in advance by means of a printing press to be used and detecting the density of a result of the printing of the color scale by means of an IRGB densitometer, solid density values $Di(\lambda)$ of individual colors (monochromatic colors, and color mixtures of two colors, three colors or four colors) of the wavelengths $\lambda$ can be obtained. Once the values of the solid density values $Di(\lambda)$ are determined, they can be utilized unless a characteristic of the printing press varies because of secular deterioration or the like.

Preferably, the target color mixture halftone density setting step includes a data acquisition step of acquiring tone values data of kcmy of a printing object picture from the outside, and a color mixture halftone density conversion step of converting the tone values of the noticed pixel regions acquired at the data acquisition step into color mixture halftone densities based on the corresponding relationship between the tone values and the color mixture halftone densities set in advance, the color mixture halftone densities of the noticed pixel regions converted at the color mixture halftone density conversion step being set as the target color mixture halftone densities. It is to be noted that the tone values data of k, c, m and y of the printing object picture can be obtained from plate making data. Further, while line ratio is available as a name corresponding to the tone values, it is a matter of course that also data (line ratio data) regarding the line ratio correspond to the tone values data.

Preferably, the corresponding relationship between the tone values and the color mixture halftone densities used at the color mixture halftone density conversion step of the target color mixture halftone density setting step is defined as a conversion table produced based on a corresponding relationship obtained in advance by printing a color scale of the Japan Color (ISO12642) or the like under the standard density or the publicly known Neugebauer expression (B) wherein solid density values Di(λ) of the wavelengths λ of the colors of I (infrared light), R (Red), G (Green), and B (Blue) are obtained in advance by printing a color scale of the Japan Color (ISO12642) or the like under the standard density and then dot gain corrected, and a color mixture halftone density is determined using the conversion table or the publicly known Neugebauer expression (B) given below which is in the dot gain corrected state:

[Expression 2]

$$10^{-Dao(\lambda)} = (1-k)(1-c)(1-m)(1-y) + k(1-c)(1-m)(1-y)10^{-Dk(\lambda)} + c(1-k)(1-m)(1-y)10^{-Dc(\lambda)} + m(1-k)(1-c)(1-y)10^{-Dm(\lambda)} + y(1-k)(1-c)(1-m)10^{-Dy(\lambda)} + kc(1-m)(1-y)10^{-Dkc(\lambda)} + km(1-c)(1-y)10^{-Dkm(\lambda)} + ky(1-c)(1-m)10^{-Dky(\lambda)} + cm(1-k)(1-y)10^{-Dcm(\lambda)} + cy(1-k)(1-m)10^{-Dcy(\lambda)} + my(1-k)(1-c)10^{-Dmy(\lambda)} + kcm(1-y)10^{-Dkcm(\lambda)} + kcy(1-m)10^{-Dkcy(\lambda)} + kmy(1-c)10^{-Dkmy(\lambda)} + cmy(1-k)10^{-Dcmy(\lambda)} + kcmy\,10^{-Dkcmy(\lambda)}$$ (B)

where

Dao(λ): target color mixture halftone density value, k, c, m, y: tone values data in a dot gain corrected state, Di(λ): solid density value of wavelength λ of each color i (extracted from color scale data), i: one of Cyan, Magenta, Yellow, Black and color mixture of them, for example, Dc: solid density value of Cyan, Dm: solid density value of Magenta, Dy: solid density value of Yellow, Dk: solid density value of Black, Dcm: two-color overlapping solid density value of Cyan and Magenta, Dcy: two-color overlapping solid density value of Cyan and Yellow, Dmy: two-color overlapping solid density value of Magenta and Yellow, Dkc: two-color overlapping solid density value of Cyan and Black, Dkm: two-color overlapping solid density value of Magenta and Black, Dky: two-color overlapping solid density value of Yellow and Black, Dcmy: three-color overlapping solid density value of Cyan, Magenta and Yellow, Dkcm: three-color overlapping solid density value of Cyan, Magenta and Black, Dkcy: three-color overlapping solid density value of Cyan, Yellow and Black, Dkmy: three-color overlapping solid density value of Magenta, Yellow and Black, Dcmyk: four-color overlapping solid density value of Cyan, Magenta, Yellow and Black, and λ: wavelength region of each of R, G, B, I, for example, R=650 nm, G=550 nm, B=450 nm, and I=800 nm.

Or, preferably the target color mixture halftone density setting step includes a data acquisition step of acquiring kcmy tone values data and an ICC profile of a printing object picture from the outside, and a color mixture halftone density conversion step of converting the tone values of the noticed pixel region into a color mixture halftone density using the ICC profile and a device profile of the IRGB densitometer, the color mixture halftone density of the noticed pixel region converted at the color mixture halftone density conversion step being set as the target color mixture halftone density.

In this instance, the device profile is a conversion table which defines a corresponding relationship among tone values, color mixture halftone densities and color coordinate values, and the color mixture halftone density conversion step includes a first color coordinate value conversion step of converting the tone values of the noticed pixel into a color coordinate value using the ICC profile, a color mixture halftone density candidate selection step of selecting a plurality of color mixture halftone density candidates corresponding to the color coordinate value of the noticed pixel using the conversion table, a second color coordinate value conversion step of converting the tone values of the noticed pixel into another color coordinate value using the conversion table, a color difference calculation step of calculating a color difference between the two color coordinate values obtained at the first and second color coordinate value conversion steps, a tone values variation amount calculation step of calculating a variation amount of the tone values corresponding to the color difference calculated at the color difference calculation step, a virtual tone values calculation step of calculating virtual tone values by adding the variation amount calculated at the tone values variation amount calculation step to the tone values of the noticed pixel region, and a selection step of referring to the conversion table to select a color mixture halftone density candidate which most corresponds to the virtual tone values calculated at the virtual tone values calculation step from among the plural color mixture halftone density candidates selected at the color mixture halftone density candidate selection step, the selected color mixture halftone density candidate being set as the color mixture halftone density of the noticed pixel region at the color mixture halftone density conversion step.

Further, preferably, at the data acquisition step, bitmap data of the printing object picture are acquired first, and then, data produced by converting the bitmap data into low-resolution data corresponding to CIP4 data is used as the kcmy halftone dot area data.

Further, preferably, at the noticed pixel region selection step, a region in which the autocorrelation is high regarding each ink color is selected in a unit of a sensor pixel of the IRGB densitometer, and the selected region is set as the noticed pixel region for each ink color.

In this instance, preferably the region in which the autocorrelation is high at the noticed pixel region selection step is all pixel groups whose autocorrelation is higher than a condition set in advance for each ink color, and, at the noticed pixel setting step, the pixel group is automatically extracted using a computer.

Meanwhile, another picture color tone controlling apparatus for a printing press comprises an ink supplying apparatus for supplying ink to individual regions divided in a printing widthwise direction, noticed pixel region selection means for selecting a noticed pixel region to be noticed as an object of color tone control in a printing picture, target color mixture halftone density setting means for setting a target color mixture halftone density regarding the noticed pixel region selected by the noticed pixel region selection step, an IRGB densitometer disposed on a traveling line of an actually printed sheet obtained by printing, color mixture halftone density measurement means for operating the IRGB densitometer to measure an actual color mixture halftone density for each noticed pixel region of the actually printed sheet, target tone values calculation means for determining target tone values for each ink color corresponding to the target color mixture halftone density based on a corresponding relationship between tone values and color mixture halftone densities set in advance, actual tone values calculation means for calculating actual tone values for each ink color corresponding to the actual color mixture halftone density based on the corresponding relationship between the tone values and the color mixture halftone densities, target monochromatic halftone density calculation means for calculating a target monochromatic halftone density corresponding to the target tone values based on a corresponding relationship between tone values and monochromatic halftone densities set in advance, actual monochromatic halftone density calculation means for calculating an actual monochromatic halftone density corresponding to the actual tone values based on the corresponding relationship between the tone values and the monochromatic halftone densities, solid density difference calculation means for calculating a solid density difference corresponding to a difference between the target monochromatic halftone density and the actual monochromatic halftone density under the target tone values based on a corresponding relationship among tone values, monochromatic halftone densities and solid densities set in advance, and ink supplying amount adjustment means for adjusting an ink supplying amount for each ink supplying unit width based on the solid density difference, the target tone values calculation means and the actual tone values calculation means being operable to acquire, as the corresponding relationship between tone values and color mixture halftone densities, solid density values $Di(\lambda)$ for wavelengths $\lambda$ of colors of I (Infrared light), R (Red), G (Green), and B (Blue) in advance, produce the publicly known extended Neugebauer expression (A) in advance wherein a Yule-Nielsen coefficient n is set to such a value that the tone values and the color mixture halftone density have a substantially linear relationship to each other, and determine the target tone values and the actual tone values using the publicly known extended Neugebauer expression (A):

[Expression 3]

$$10^{-Da(\lambda)/n} = (1-K)(1-c)(1-m)(1-y) + k(1-c)(1-m)(1-y)$$
$$10^{-Dk(\lambda)/n} + c(1-k)(1-m)(1-y)10^{-Dc(\lambda)/n} + m(1-k)$$
$$(1-c)(1-y)10^{-Dm(\lambda)/n} + y(1-k)(1-c)(1-m)$$
$$10^{-Dy(\lambda)/n} + kc(1-m)(1-y)10^{-Dkc(\lambda)/n} + km(1-c)(1-$$
$$y)10^{-Dkm(\lambda)/n} + ky(1-c)(1-m)10^{-Dky(\lambda)/n} + cm(1-k)$$
$$(1-y)10^{-Dcm(\lambda)/n} + cy(1-k)(1-m)10^{-Dcy(\lambda)/n} + my$$
$$(1-k)(1-c)10^{-Dmy(\lambda)/n} + kcm(1-y)10^{-Dkcm(\lambda)/n} + kcy$$
$$(1-m)10^{-Dkcy(\lambda)/n} + kmy(1-c)10^{-Dkmy(\lambda)/n} + cmy(1-$$
$$k)10^{-Dcmy(\lambda)/n} + kcmy10^{-Dkcmy(\lambda)/n} \quad (A)$$

where
$Da(\lambda)$: color mixture halftone density value,
k, c, m, y: tone values of corresponding inks,
$Di(\lambda)$: solid density value of wavelength $\lambda$ of each color i (extracted from color scale data),
i: one of Cyan, Magenta, Yellow, Black and color mixture of them,
for example, Dc: solid density value of Cyan, Dm: solid density value of Magenta,
Dy: solid density value of Yellow, Dk: solid density value of Black,
Dcm: two-color overlapping solid density value of Cyan and Magenta
Dcy: two-color overlapping solid density value of Cyan and Yellow
Dmy: two-color overlapping solid density value of Magenta and Yellow,
Dkc: two-color overlapping solid density value of Cyan and Black,
Dkm: two-color overlapping solid density value of Magenta and Black
Dky: two-color overlapping solid density value of Yellow and Black,
Dcmy: three-color overlapping solid density value of Cyan, Magenta and Yellow,
Dkcm: three-color overlapping solid density value of Cyan, Magenta and Black,
Dkcy: three-color overlapping solid density value of Cyan, Yellow and Black,
Dkmy: three-color overlapping solid density value of Magenta, Yellow and Black,
Dcmyk: four-color overlapping solid density value of Cyan, Magenta, Yellow and Black
$\lambda$: wavelength region of each of R, G, B, I, for example, R=650 nm, G=550 nm, B=450 nm, I=800 nm, and
n: coefficient of Yule-Nielsen.

Preferably, the solid density value $Di(\lambda)$ for each of the wavelengths $\lambda$ of the colors of I (infrared light), R (Red), G (Green) and B (Blue) in the publicly known extended Neugebauer expression (A) is acquired from data obtained in advance by printing a color scale of the Japan Color (ISO12642) or the like under the standard density.

Further, preferably the target color mixture halftone density setting means includes data acquisition means for acquiring tone values data of kcmy of a printing object picture from the outside, and color mixture halftone density conversion means for converting the tone values of the noticed pixel region acquired by the data acquisition means into color mixture halftone density based on the corresponding relationship between the tone values and the color mixture halftone densities set in advance, the color mixture halftone density of the noticed pixel region converted by the color mixture halftone density conversion means being set as the target color mixture halftone density. It is to be noted that the tone values data of k, c, m and y of the printing object picture can be obtained from plate making data. Further, while line ratio is available as a name corresponding to the tone values, it is a matter of course that also data (line ratio data) regarding the line ratio correspond to the tone values data.

In this instance, preferably the corresponding relationship between the tone values and the color mixture halftone densities used by the color mixture halftone density conversion means is defined as a conversion table produced based on a corresponding relationship obtained in advance by printing a color scale of Japan Color (ISO12642) or the like under the standard density or the publicly known Neugebauer expression (B) wherein solid density values Di(λ) of the wavelengths λ of the colors of I (infrared light), R (Red), G (Green), and B (Blue) are obtained in advance by printing a color scale of the Japan Color (ISO12642) or the like under the standard density and then dot gain corrected, and a color mixture halftone density is determined using the conversion table or the publicly known Neugebauer expression (B) in the dot gain corrected state:

[Expression 4]

$$10^{-Dao(\lambda)} = (1-k)(1-c)(1-m)(1-y) + k(1-c)(1-m)(1-y)10^{-Dk(\lambda)} + c(1-k)(1-m)(1-y)10^{-Dc(\lambda)} + m(1-k)(1-c)(1-y)10^{-Dm(\lambda)} + y(1-k)(1-c)(1-m)10^{-Dy(\lambda)} + kc(1-m)(1-y)10^{-Dkc(\lambda)} + km(1-c)(1-y)10^{-Dkm(\lambda)} + ky(1-c)(1-m)10^{-Dky(\lambda)} + cm(1-k)(1-y)10^{-Dcm(\lambda)} + cy(1-k)(1-m)10^{-Dcy(\lambda)} + my(1-k)(1-c)10^{-Dmy(\lambda)} + kcm(1-y)10^{-Dkcm(\lambda)} + kcy(1-m)10^{-Dkcy(\lambda)} + kmy(1-c)10^{-Dkmy(\lambda)} + cmy(1-k)10^{-Dcmy(\lambda)} + kcmy \cdot 10^{-Dkcmy(\lambda)} \quad (B)$$

where

Dao(λ): target color mixture halftone density value, k, c, m, y: tone values data in a dot gain corrected state, Di(λ): solid density value of wavelength λ of each color i (extracted from color scale data), i: one of Cyan, Magenta, Yellow, Black and color mixture of them, for example, Dc: solid density value of Cyan, Dm: solid density value of Magenta, Dy: solid density value of Yellow, Dk: solid density value of Black, Dcm: two-color overlapping solid density value of Cyan and Magenta, Dcy: two-color overlapping solid density value of Cyan and Yellow, Dmy: two-color overlapping solid density value of Magenta and Yellow, Dkc: two-color overlapping solid density value of Cyan and Black, Dkm: two-color overlapping solid density value of Magenta and Black, Dky: two-color overlapping solid density value of Yellow and Black, Dcmy: three-color overlapping solid density value of Cyan, Magenta and Yellow, Dkcm: three-color overlapping solid density value of Cyan, Magenta and Black, Dkcy: three-color overlapping solid density value of Cyan, Yellow and Black, Dkmy: three-color overlapping solid density value of Magenta, Yellow and Black, Dcmyk: four-color overlapping solid density value of Cyan, Magenta, Yellow and Black, and λ: wavelength region of each of R, G, B, I, for example, R=650 nm, G=550 nm, B=450 nm, and I=800 nm.

Preferably, the picture color tone controlling apparatus for a printing press further comprises noticed pixel region selection means for automatically extracting, as the noticed pixel region for each ink color, all pixel groups whose autocorrelation is higher than a condition set in advance for each ink color.

Effects of the Invention

With the picture color tone controlling method and apparatus for a printing press of the present invention, since color tone control can be performed using not a spectrometer but an IRGB densitometer, the cost required for the measuring system can be reduced, and besides the picture color tone controlling method and apparatus can be applied sufficiently also to a high speed printing press such as a rotary press for newspapers.

Particularly, when the actual tone values are determined from the actual color mixture halftone density and when the target tone values are determined from the target color mixture halftone density, the publicly known expanded Neugebauer expression (A) is used wherein the solid density values Di(λ) of the wavelengths λ of the colors of I (Infrared radiation), R (Red), G (Green), B (Blue) are acquired in advance as a corresponding relationship between the tone values and the color mixture halftone density and the Yule-Nielsen coefficient n is set to such a value that the relationship between the tone values and the color mixture halftone density value becomes substantially linear. Therefore, the corresponding relationship in the color space can be easily extended to the outside of the color space. Therefore, conversion from a color mixture halftone density into tone values can be performed with certainty also with regard to the outside region of the color space defined with respect to the standard density. For example, even if printing is performed with a density which exceeds the color space defined with the standard density, the actual tone values can be determined with certainty and the color tone control can be performed.

Further, when the target color mixture halftone density is set, where tone values data of kcmy of a printing object picture are acquired and the tone values of the data are converted into a color mixture halftone density and then the converted color mixture halftone density of the noticed pixel region is set as the target color mixture halftone density, if a conversion table produced based on a corresponding relationship obtained in advance by printing a color scale of the Japan Color (ISO12642) or the like under the standard density or the publicly known Neugebauer expression (B) wherein solid density values Di(λ) of the wavelengths λ of the colors of I (infrared light), R (Red), G (Green), and B (Blue) are obtained in advance by printing a color scale of the Japan Color (ISO12642) or the like under the standard density and then dot gain corrected is used, then the target color mixture halftone density can be determined with a high degree of accuracy.

Where kcmy tone values data of a printing object picture can be acquired from the outside and also an ICC profile can be acquired in addition to the kcmy tone values data from the outside, the color tone can be controlled based on the ICC profile acquired from the printing requesting source or the like and a printed matter of a color tone desired by the printing requesting source can be obtained readily.

Further, a noticed pixel region can be set readily by arithmetically operating and automatically extracting a pixel which has the highest density sensitivity for each ink color or a pixel which has the highest autocorrelation to the tone values of each pixel for each ink color and setting the extracted pixel as a noticed pixel region.

Figure 1:
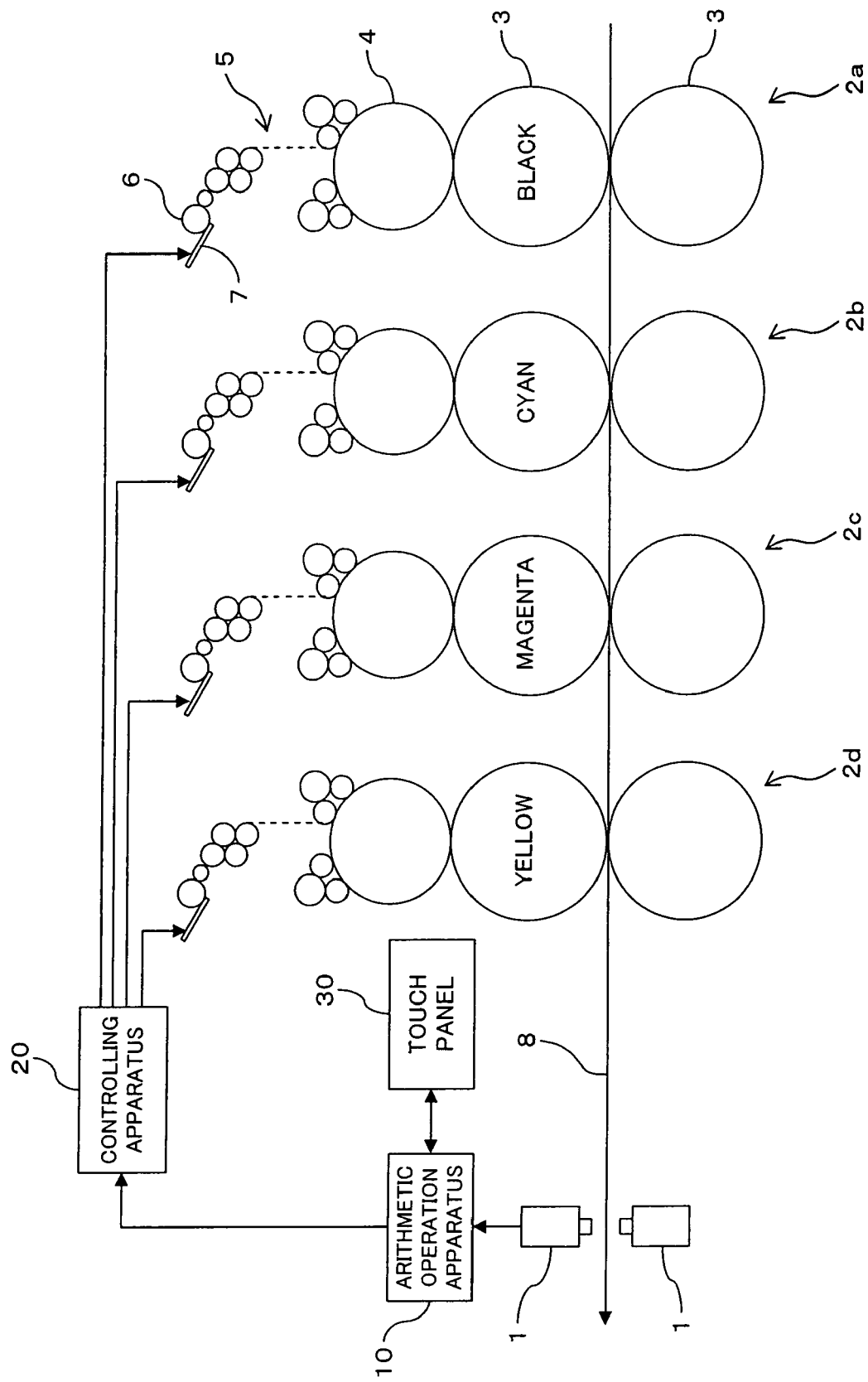
FIG. 1 is a view schematically showing a general configuration of an offset rotary press for newspapers according to a first embodiment of the present invention.

DESCRIPTION OF REFERENCE CHARACTERS 1 line sensor type IRGB densitometer
2a, 2b, 2c, 2d printing unit
3 blanket cylinder
4 printing cylinder
5 ink roller group
6 ink fountain roller
7 ink key
8 printing sheet
10 arithmetic operation apparatus
11 DSP
12 PC
14 color conversion section
15 ink supplying amount arithmetic operation section
16 online controlling section
17 key opening limiter arithmetic operation section
20 control built in printing press
30 touch panel

BEST MODE FOR CARRYING OUT THE INVENTION

In the following, preferred embodiments of the present invention are described with reference to the accompanying drawings.

(A) First Embodiment

FIG. 1 shows a general configuration of an offset rotary press for newspapers according to a first embodiment of the present invention. The offset rotary press for newspapers of the present embodiment is a double-sided printing press for multi-color printing and includes printing units 2a, 2b, 2c and 2d disposed for different ink colors [black (k), cyan (c), magenta (m) and yellow (y)] along a transport path of a printing sheet 8. In the present embodiment, each of the printing units 2a, 2b, 2c and 2d includes an ink supplying apparatus of the ink key type which includes a plurality of ink keys 7 and an ink fountain roller 6. In the ink supplying apparatus of the type described, the ink supplying amount can be adjusted by the gap amount (the gap amount is hereinafter referred to as ink key opening) of each of the ink keys 7 from the ink fountain roller 6. The ink keys 7 are juxtaposed in the printing widthwise direction, and the ink supplying amount can be adjusted in a unit of the width of each of the ink keys 7 (the ink supplying unit width by each ink key 7 is hereinafter referred to as key zone). The ink whose supplying amount is adjusted by each ink key 7 is kneaded to a suitable degree to form a thin film in an ink roller group 5 and then supplied to a printing surface of a printing cylinder 4. Then, the ink sticking to the printing face is transferred as a picture to the printing sheet 8 through a blanket cylinder 3. It is to be noted that, though not shown in FIG. 1, since the offset rotary press for newspapers of the present embodiment is for double-sided printing, each of the printing units 2a, 2b, 2c and 2d includes a pair of blanket cylinders 3, 3 disposed across the transport path of the printing sheet 8, and a printing cylinder 4 and an ink supplying apparatus are provided for each of the blanket cylinders 3.

The offset rotary press for newspapers includes a pair of line sensor type IRGB densitometers 1 on the further downstream of the most downstream printing units 2d. Each of the line sensor type IRGB densitometers 1 is a measuring instrument for measuring a color of a picture on the printing sheet 8 as reflection densities (color mixture halftone densities) of I (infrared radiation), R (red), G (green) and B (blue) on a line in the printing widthwise direction. The offset rotary press for newspapers can measure the reflection density over the overall printing sheet 8 or measure the reflection density at an arbitrary position of the printing sheet 8. Since the offset rotary press for newspapers is for double-sided printing, the line sensor type IRGB densitometers 1 are disposed on the opposite front and rear sides across the transport path of the printing sheet 8 so that they can measure the reflection density on the opposite front and rear faces of the printing sheet 8.

Figure 2:
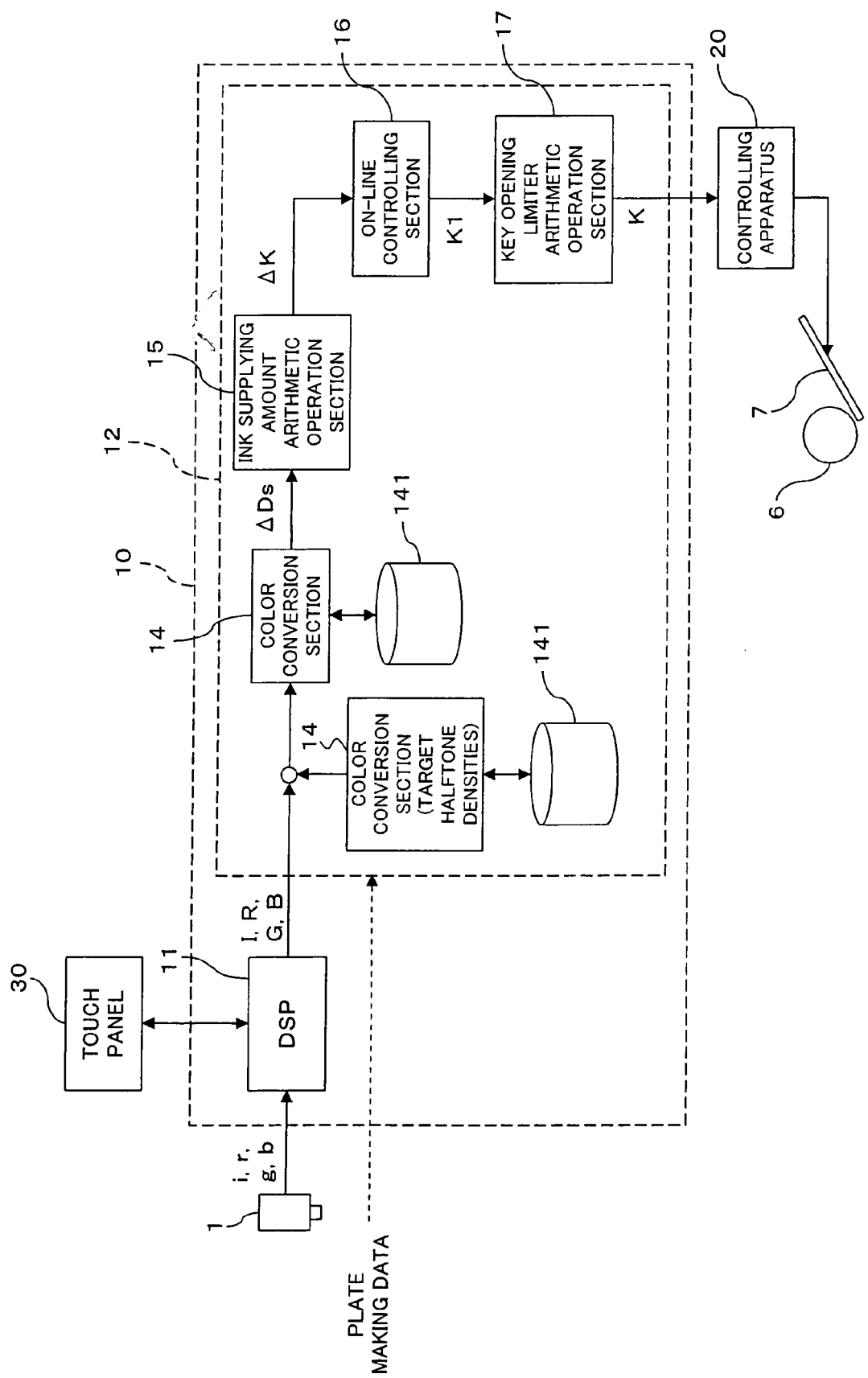
FIG. 2 is a functional block diagram showing a color tone controlling function of an arithmetic operation apparatus of FIG. 1.

The reflection densities measured by the line sensor type IRGB densitometers 1 are transmitted to an arithmetic operation apparatus 10. The arithmetic operation apparatus 10 is an apparatus for arithmetically operating control data of the ink supplying amount, and performs arithmetic operation based on the reflection densities measured by the line sensor type IRGB densitometers 1 to arithmetically operate the opening of each of the ink keys 7 for making the color of the picture of the printing sheet 8 coincide with a target color. Here, FIG. 2 is a view showing a general configuration of a picture color tone controlling apparatus for the offset rotary press for newspapers according to the embodiment of the present invention and simultaneously is a functional block diagram showing the arithmetic operation apparatus 10 with attention paid to a color tone controlling function.

The arithmetic operation apparatus 10 includes a DSP (digital signal processor) 11 and a PC (personal computer) 12 disposed separately from the printing press. The PC 12 has functions as a color conversion section 14, an ink supplying amount arithmetic operation section 15, an online controlling section 16 and a key opening limiter arithmetic operation section 17 allocated thereto. The line sensor type IRGB densitometers 1 are connected to the input side of the arithmetic operation apparatus 10, and a controlling apparatus 20 built in the printing press is connected to the output side of the arithmetic operation apparatus 10. The controlling apparatus 20 functions as ink supplying amount adjusting means for adjusting the ink supplying amount for each of the key zones of the ink keys 7. The controlling apparatus 20 controls an opening/closing apparatus not shown for opening and closing each of the ink keys 7 and can adjust the key opening independently for each ink key 7 of each of the printing units 2a, 2b, 2c and 2d. Further, a touch panel 30 as a display apparatus is connected to the arithmetic operation apparatus 10. The touch panel 30 can be used to display a printing surface of the printing sheet 8 whose image is picked up by the line sensor type IRGB densitometer 1 and select an arbitrary region on the printing surface with a finger.

Figure 3:
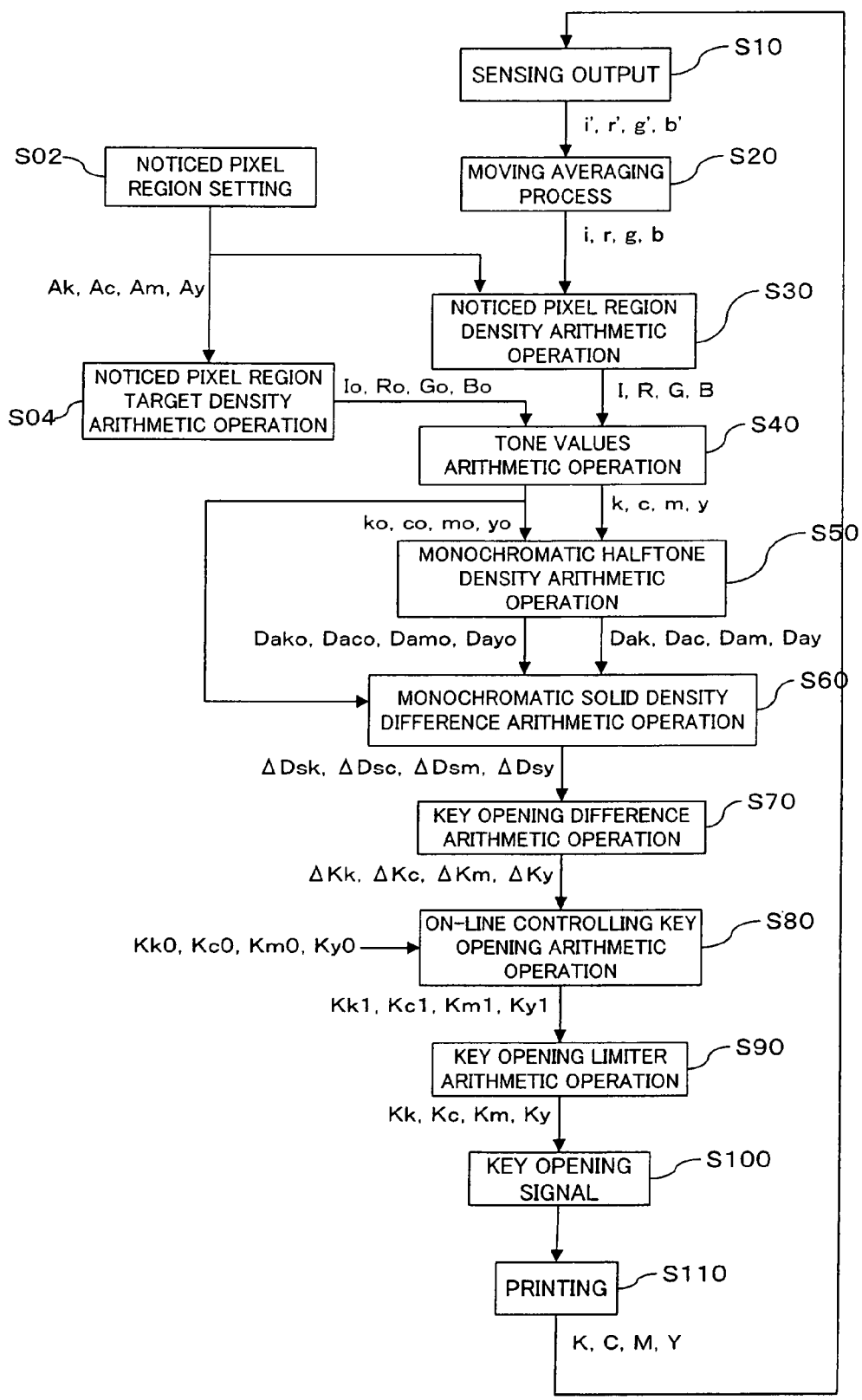
FIG. 3 is a flow chart illustrating a processing flow of color tone control by the arithmetic operation apparatus of FIG. 1.

FIG. 3 is a view illustrating a processing flow of color tone control by the arithmetic operation apparatus 10. In the following, the processing substance of color tone control by the arithmetic operation apparatus 10 is described principally with reference to FIG. 3.

It is to be noted that, before the color tone control is performed, solid density values Di($\lambda$) of wavelengths $\lambda$ of I (infrared radiation), R (red), G (green), B (blue) are acquired from data obtained in advance by printing a color scale of the Japan Color (ISO12642) or the like in the standard density. In particular, a color scale of the Japan Color (ISO12642) or the like is printed in advance in the standard density using a printing press to be used, and the density is detected by the IRGB densitometer based on the printing result of the color scale. Consequently, the solid density value Di($\lambda$) of each color (each of monochromes and color mixtures of two, three or four colors) of the wavelength $\lambda$ can be acquired. As long as the characteristic of the printing press is not varied by secular degradation or the like, the solid density values Di($\lambda$) can be utilized after the determination is performed once.

Further, plate making data are inputted in advance to the arithmetic operation apparatus 10, and the arithmetic operation apparatus 10 acquires k, c, m, y data of each pixel from the plate making data in advance.

In the color tone control, a noticed pixel region (hereinafter referred simply also as noticed point) is set first (step S02), and the process of the color tone control is performed based on the set noticed pixel region.

Automatic setting of the noticed pixel region is described. Plate making data is inputted in advance to the arithmetic operation apparatus 10, and the DSP 11 of the arithmetic operation apparatus 10 selects a region having a high autocorrelation for each ink color from among kcmy tone values data obtained based on the plate making data. Then the selected region is automatically set as the noticed pixel region corresponding to each ink color for each ink color.

It is to be noted that, while the plate making data are given as bitmap data, in order to set a noticed pixel region, the bitmap data are converted into low-resolution data equivalent to CIP4 data according to the format of the printing press and then a process is performed in a unit of a pixel of a sensor described below.

In particular, the region having a high autocorrelation for each ink color is a region in which the autocorrelation sensitivity H has a value higher than a predetermined value set in advance and is a region of a pixel unit of the sensor (IRGB densitometer) 1. The pixel unit of the sensor is a minimum unit of the resolution of the sensor (IRGB densitometer) 1. In particular, a pixel group formed by collecting a great number of pixels of the plate making data corresponds to one pixel (one block) of the sensor pixel unit. For example, where the low-resolution data of the CIP4 are of 50.8 dpi and the resolution of 1 block of the sensor 1 is 25.4 dpi, a region of 2 pixels in the vertical direction by 2 pixels in the horizontal direction (in the pixel unit of the plate making data, 2×2=4 pixels) is one pixel unit of the sensor pixel unit.

The autocorrelation sensitivities H, for example, the autocorrelation sensitivity Hc of cyan, can be represented as "Hc=$c^p$/(c+m+y+k)" using pixel area ratio data (c, m, y, k). Where the value of the autocorrelation sensitivity Hc is compared with a reference autocorrelation sensitivity value (predetermined value) $H_0$ set in advance, if the value of the autocorrelation sensitivity Hc is higher than the reference autocorrelation sensitivity value $H_0$, then it is determined that the region has a high autocorrelation with regard to cyan.

Similarly, also with regard to different ink colors, the value of the autocorrelation sensitivity H is arithmetically operated and individually compared with the reference autocorrelation sensitivity value (predetermined value) $H_0$ set in advance. It is to be noted that p is an exponentiation of the autocorrelation, and, for example, approximately 1.3 is selected as the value of the exponent value p.

It is to be noted that the reference autocorrelation sensitivity value $H_0$ can be set by inputting operation of the operator. Therefore, it is possible to set the reference autocorrelation sensitivity value $H_0$ to a rather high value to set the noticed pixel region restrictively to a region having a considerably high autocorrelation so that the density detection sensitivity is raised from a point which is of the pertaining ink and has a high tone thereby to raise the accuracy of the color tone control although the noticed pixel region decreases. Or, it is possible to set the reference autocorrelation sensitivity value $H_0$ to a rather low value to set the noticed pixel region including even a region in which the autocorrelation is not very high so that the noticed pixel region is expanded thereby to raise the accuracy of the color tone control although the density detection sensitivity drops. Naturally, a recommendable value (for example, an average autocorrelation value over the entire picture) of the reference autocorrelation sensitivity value $H_0$ is inputted in advance, and an unskilled operator can utilize the recommendable value. Further, in principle, while the reference autocorrelation sensitivity value $H_0$ is commonly used for the different ink colors, also it is a possible idea to make the reference autocorrelation sensitivity value $H_0$ different among the different ink colors.

Then, a target color mixture halftone density is set for the set noticed pixel region of each ink (step S04). In particular, the arithmetic operation apparatus 10 has tone values (or line ratio) Ak, Ac, Am, Ay data of the noticed pixel regions acquired based on the plate making data. Further, the color conversion section 14 of the PC 12 includes a database 141 for coordinating the tone values and color mixture halftone densities of the individual ink colors with each other. The database 141 is produced with reference to data [conversion table which defines a corresponding relationship among tone values (k, c, m, y), color mixture halftone densities (I, R, G, B), and color coordinate values (L, a, b) of the standard colors] obtained by printing a printed matter under the newspaper printing Japan Color (ISO12642) standard established by the ISO/TC130 national commission and actually measuring the printed pattern by an IRGB densitometer. The color conversion section 14 determines color mixture halftone densities corresponding to the inputted line ratios Ak, Ac, Am, Ay for each key zone and sets the determined color mixture halftone densities as target color mixture halftone densities Io, Ro, Go, Bo.

It is to be noted that, if the dot gain is taken into consideration, then even if printing pictures have the same line ratios Ak, Ac, Am, Ay, the density value in color development differs depending upon the degree of density (50% plane halftone, 80% plane halftone, solid and so forth) of the halftone which forms the printing picture. Therefore, the color conversion section 14 is configured such that it can variably adjust the dot gain for each degree of density of the halftone and can set the target color mixture halftone densities Io, Ro, Go, Bo with the dot gain taken into consideration using a parameter determined based on the dot gain used as a function as the parameter to be used when the line ratios Ak, Ac, Am, Ay are converted into the color mixture halftone densities Io, Ro, Go, Bo.

After the target color mixture halftone densities Io, Ro, Go, Bo are set in such a manner as described above, printing is started and processes at steps beginning with step S10 are executed repetitively. First, at step S10, the line sensor type IRGB densitometer 1 measures the reflected light amounts i', r', g', b' of each of the pixels on the overall face of the overall printing sheet 8. The reflected light amounts i', r', g', b' of the pixels measured by the IRGB densitometer 1 are inputted to the DSP 11.

The DSP 11 performs, at step S20, moving averaging in a unit of a predetermined number of prints with regard to the reflected light amounts i', r', g', b' of the pixels to arithmetically operate reflected light amounts i, r, g, b of the pixels from which noise components are removed. Then, at step S30, the reflected light amounts i, r, g, b are averaged for each key zone to arithmetically operate color mixture halftone densities (actual color mixture halftone densities) I, R, G, B with reference to a reflected light amount at a blank portion. For example, where the reflected light amount of infrared radiation at a blank portion is represented by ip and an average reflected light amount of the infrared radiation in the key zones is represented by ik, the actual color mixture halftone density I of the infrared radiation can be determined from I=$\log_{10}$(ip/ik). The color mixture halftone densities I, R, G, B of each noticed pixel region arithmetically operated by the DSP 11 are inputted to the color conversion section 14 of the PC 12.

The color conversion section 14 performs the processes at steps S40, S50 and S60. First, at step S40, the target color mixture halftone densities Io, Ro, Go, Bo set at step S04 and the tone values of each ink color corresponding to the actual color mixture halftone densities I, R, G, B arithmetically operated at step S30 are arithmetically operated individually. The database 141 is used for the arithmetic operations, and the tone values of each ink color corresponding to the target color mixture halftone densities Io, Ro, Go, Bo are arithmetically operated as target tone values ko, co, mo, yo and the tone values of each ink color corresponding to the actual color mixture halftone densities I, R, G, B are arithmetically operated as actual tone values k, c, m, y.

Here, to the database 141, not only the conversion table [hereinafter referred to sometimes as look-up table (LUT)] produced based on the printing result obtained by printing the color scale of the Japan Color (ISO12642) or the like under the standard density is inputted as described hereinabove. Meanwhile, also a publicly known expanded Neugebauer expression which is produced based on the printing result described above and wherein the Nielsen coefficient (coefficient of Yule-Nielsen) n is set to a value (for example, n≧approximately 100) with which the relationship between the tone values and the color mixture halftone density value becomes substantial linear is inputted.

[Expression 5]

$$10^{-Da(\lambda)/n} = (1-K)(1-c)(1-m)(1-y) + k(1-c)(1-m)(1-y)10^{-Dk(\lambda)/n} + c(1-k)(1-m)(1-y)10^{-Dc(\lambda)/n} + m(1-k)(1-c)(1-y)10^{-Dm(\lambda)/n} + y(1-k)(1-c)(1-m)10^{-Dy(\lambda)/n} + kc(1-m)(1-y)10^{-Dkc(\lambda)/n} + km(1-c)(1-y)10^{-Dkm(\lambda)/n} + ky(1-k)(1-y)10^{-Dky(\lambda)/n} + cm(1-k)(1-y)10^{-Dcm(\lambda)/n} + cy(1-k)(1-m)10^{-Dcy(\lambda)/n} + my(1-k)(1-c)10^{-Dmy(\lambda)/n} + kcm(1-y)10^{-Dkcm(\lambda)/n} + kcy(1-m)10^{-Dkcy(\lambda)/n} + kmy(1-c)10^{-Dkmy(\lambda)/n} + cmy(1-k)10^{-Dcmy(\lambda)/n} + kcmy10^{-Dkcmy(\lambda)/n} \quad (A)$$

where

Da($\lambda$): color mixture halftone density value, k, c, m, y: tone values of corresponding inks, Di($\lambda$): solid density value of wavelength $\lambda$ of each color i (extracted from color scale data), i: one of Cyan, Magenta, Yellow, Black and color mixture of them, for example, Dc: solid density value of Cyan, Dm: solid density value of Magenta, Dy: solid density value of Yellow, Dk: solid density value of Black, Dcm: two-color overlapping solid density value of Cyan and Magenta, Dcy: two-color overlapping solid density value of Cyan and Yellow, Dmy: two-color overlapping solid density value of Magenta and Yellow, Dkc: two-color overlapping solid density value of Cyan and Black, Dkm: two-color overlapping solid density value of Magenta and Black Dky: two-color overlapping solid density value of Yellow and Black, Dcmy: three-color overlapping solid density value of Cyan, Magenta and Yellow, Dkcm: three-color overlapping solid density value of Cyan, Magenta and Black, Dkcy: three-color overlapping solid density value of Cyan, Yellow and Black, Dkmy: three-color overlapping solid density value of Magenta, Yellow and Black, Dcmyk: four-color overlapping solid density value of Cyan, Magenta, Yellow and Black $\lambda$: wavelength region of each of R, G, B, I, for example, R=650 nm, G=550 nm, B=450 nm, I=800 nm, and n: coefficient of Yule-Nielsen.

It is to be noted that c, m, y, k, kc, km, ky, cm, cy, my, kcm, kcy, kmy, cmy and kcmy in the expression (A) indicate the halftone dot ratios of the colors (monochromes or color mixtures). Regarding the color mixtures, for example, kc indicates the product of the tone values of black (k) and cyan (c), and, for example, kcmy indicates the product of black (k), cyan (c), magenta (m) and yellow (y).

Further, Dkc($\lambda$), Dkm($\lambda$), . . . , Dkcmy($\lambda$) [solid density value Di($\lambda$) of the wavelength $\lambda$ of each color i] in the expression (A) individually indicate each a solid overlapping density value of the wavelength $\lambda$ in the target density value for each ink color. For example, Dkc($\lambda$) indicates a density value of the wavelength $\lambda$ in the overlapping target density value of each color in the color mixture between black (k) and cyan (c), and, for example, Dkcmy($\lambda$) indicates a density value of the wavelength $\lambda$ in the overlapping target density value of each color in the color mixture among black (k), cyan (c), magenta (m), and yellow (y). It is to be noted that $\lambda$ indicates the wavelength of I, R, G, or B. The Di($\lambda$) values are determined in advance as described above.

Figure 4:
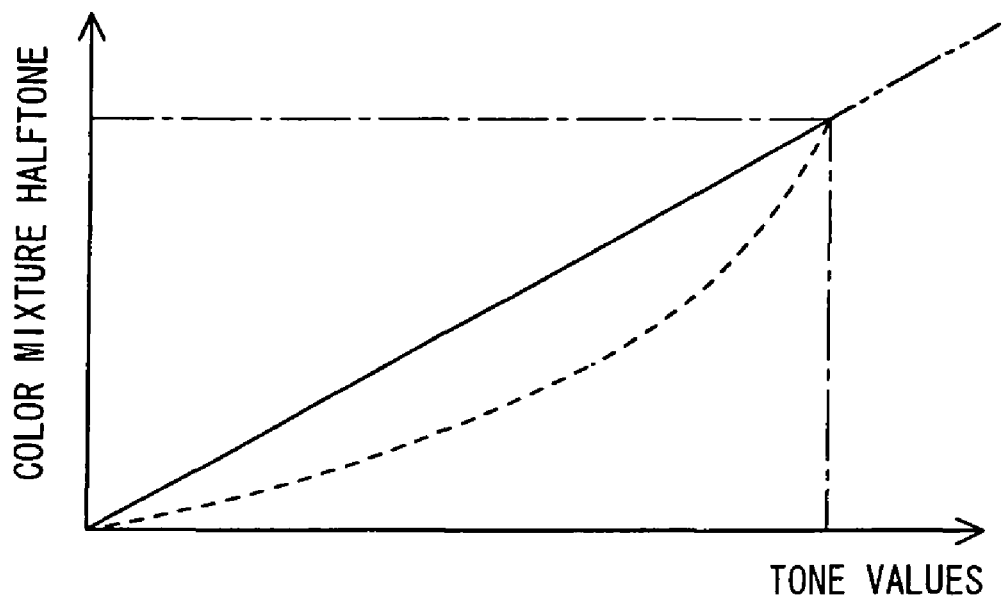
FIG. 4 is a view illustrating expansion of a color space according to the first embodiment of the present invention.

Also in the publicly known Neugebauer expression or the expanded Neugebauer expression, if the Nielsen coefficient n is not suitably set, then the relationship between the tone values and the color mixture halftone density normally exhibits a curve as indicated by a broken line in FIG. 4. It is to be noted that, while the example of FIG. 4 is a section where, as an example, the tone values are fixed to c=m=y=0 and the relationship between the monochromatic tone values of k and the color mixture halftone density is plotted, such a non-linear relationship as shown in FIG. 4 appears also in a multi-dimensional space. On the other hand, where the publicly known expanded Neugebauer expression (A) wherein the Nielsen coefficient n is set to a value with which a substantially linear relationship is obtained between the tone values and the color mixture halftone density is used, the relationship between the tone values and the color mixture halftone density becomes such a linear relationship as indicated by a full line in FIG. 4. Such a linear relationship as shown in FIG. 4 appears also in a multi-dimensional space.

Figure 5:
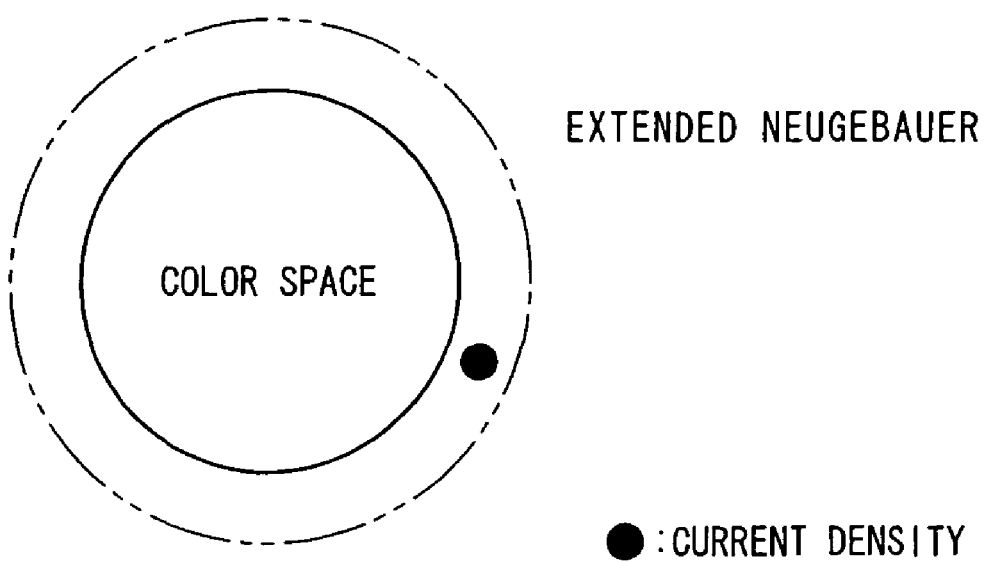
FIG. 5 is a view showing a corresponding relationship between tone values and a color mixture halftone density according to the first embodiment of the present invention.

Accordingly, as seen from a region limit indicated by an alternate long and short dash line in FIG. 5, the relationship between the tone values and the color mixture halftone density in a color space region assumed with respect to the reference density can be easily extended and applied to an outer side region of the color space as indicated by an alternate long and two dashes line in FIG. 5. In particular, the relationship between the tone values and the color mixture halftone density can be applied also to the outside space to the color space region indicated by a full line circle in FIG. 5, and the color space can be substantially extended as indicated by an alternate long and two dashes line circle in FIG. 5 while the relationship between the tone values and the color mixture halftone density is set with respect to the reference density.

Figure 6:
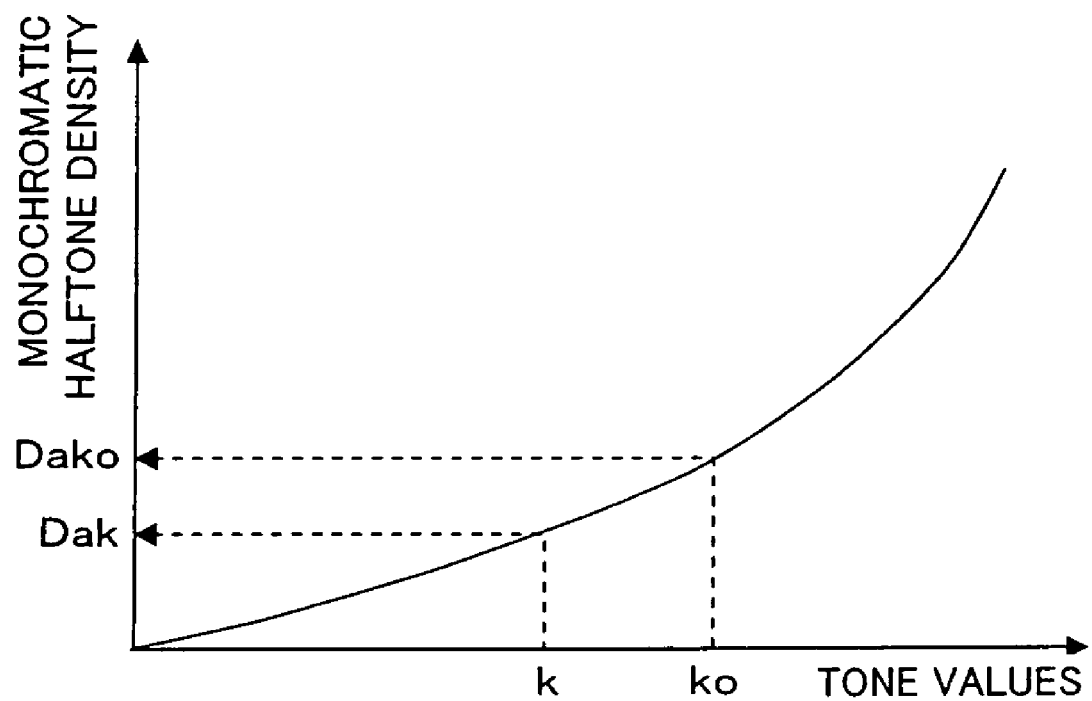
FIG. 6 is a map illustrating a corresponding relationship of a monochromatic halftone density with the tone values.

Next, the color conversion section 14 arithmetically operates monochromatic halftone densities of the ink colors corresponding to the target tone values ko, co, mo, yo and the actual tone values k, c, m, y at step S50. Such a map as shown in FIG. 6 is used for the arithmetic operation. FIG. 6 shows an example of a map wherein the monochromatic halftone density measured where the tone values are varied is plotted as a characteristic curve, and the map is produced from data measured in advance. In the example shown in FIG. 6, by collating the target tone values ko and the actual tone values k of black with the map, a target monochromatic halftone density Dako and an actual monochromatic halftone density Dak are determined from the characteristic curve in the map. As described above, the color conversion section 14 determines target monochromatic halftone densities Dako, Daco, Damo, Dayo and actual monochromatic halftone densities Dak, Dac, Dam, Day of the ink colors.

Figure 7:
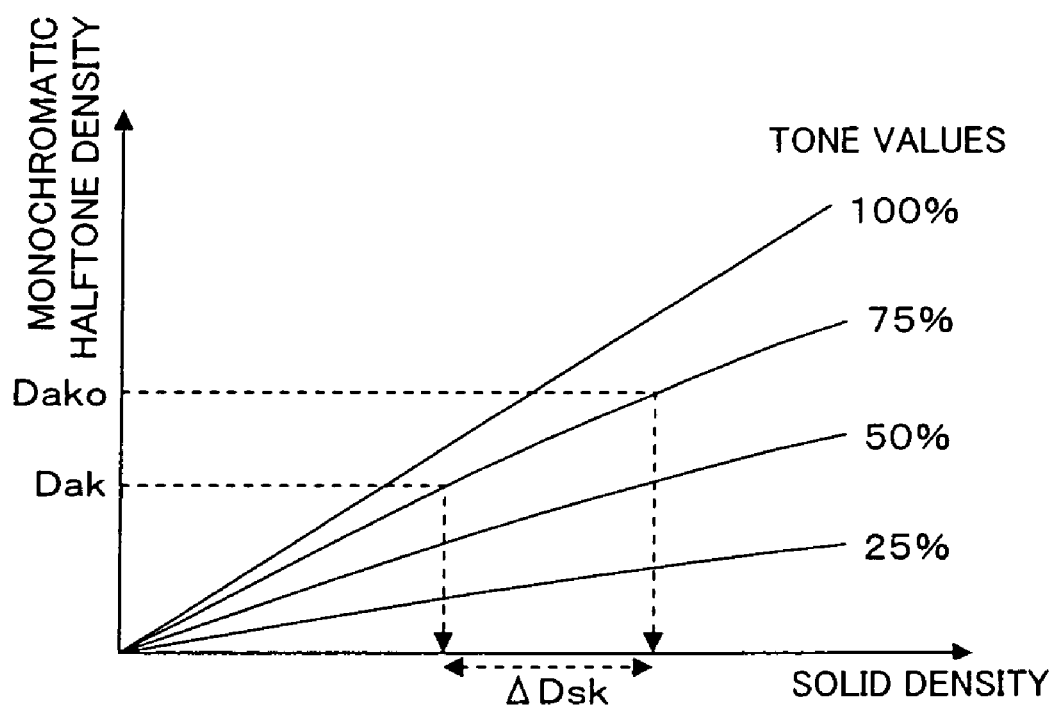
FIG. 7 is a map illustrating a corresponding relationship of a solid density with the tone values and the monochromatic halftone density.

Then, at step S60, the color conversion section 14 arithmetically operates solid density differences $\Delta Dsk$, $\Delta Dsc$, $\Delta Dsm$, $\Delta Dsy$ of the ink colors corresponding to differences between the target monochromatic halftone densities Dako, Daco, Damo, Dayo and the actual monochromatic halftone densities Dak, Dac, Dam, Day. It is to be noted that the solid density depends also on the tone values, and, with regard to the monochromatic halftone density, the solid density decreases as the tone values increase. Therefore, the color conversion section 14 performs arithmetic operation using such a map as shown in FIG. 7. FIG. 7 shows an example of a map where the monochromatic halftone density actually measured where the monochromatic solid density is varied is plotted as a characteristic curve for each tone value, and the map is produced from data measured in advance. The color conversion section 14 selects the characteristic curves corresponding to the target tone values ko, co, mo, yo of the ink colors from within the map shown in FIG. 7, and determines the solid density differences $\Delta Dsk$, $\Delta Dsc$, $\Delta Dsm$, $\Delta Dsy$ by applying the target monochromatic halftone densities Dako, Daco, Damo, Dayo and the actual monochromatic halftone densities Dak, Dac, Dam, Day to the selected characteristic curves. In the example shown in FIG. 7, if the target monochromatic halftone density Dako and the actual monochromatic halftone density Dak are collated with the map where the target tone value of black is 75%, then the solid density difference $\Delta Dsk$ of black is determined from within the 75% characteristic curve in the map.

The solid density differences $\Delta Dsk$, $\Delta Dsc$, $\Delta Dsm$, $\Delta Dsy$ of the individual ink colors arithmetically operated by the color conversion section 14 are inputted to the ink supplying amount arithmetic operation section 15. At step S70, the ink supplying amount arithmetic operation section 15 arithmetically operates key opening difference amounts $\Delta Kk$, $\Delta Kc$, $\Delta Km$, $\Delta Ky$ corresponding to the solid density differences $\Delta Dsk$, $\Delta Dsc$, $\Delta Dsm$, $\Delta Dsy$, respectively. The key opening difference amounts $\Delta Kk$, $\Delta Kc$, $\Delta Km$, $\Delta Ky$ are increasing or decreasing amounts from the key openings Kk0, Kc0, Km0, Ky0 at present (key openings Kk, Kc, Km, Ky outputted to the controlling apparatus 20 of the printing press by the process at step S100 in the preceding operation cycle) of the individual ink keys 7, and the ink supplying amount arithmetic operation section 15 performs the arithmetic operation using the known API function (auto-preset inking function). The API function is a function indicating a relationship between image area ratios A (Ak, Ac, Am, Ay) and the key openings K (Kk, Kc, Km, Ky) for each key zone to establish a reference density. The image area ratios A determined at step S0 may be used as such. More particularly, the ink supplying amount arithmetic operation section 15 determines the ratios kd (kd=$\Delta Ds$/Ds) of the solid density differences $\Delta Ds$ ($\Delta Dsk$, $\Delta Dsc$, $\Delta Dsm$, $\Delta Dsy$) to reference densities Ds (Dsk, Dsc, Dsm, Dsy) and the key opening K for obtaining a reference density with respect to each of the image area ratios A using the API function. Then, the ink supplying amount arithmetic operation section 15 determines the product of the image area ratios A and the key openings K to determine key opening difference amounts $\Delta K$ ($\Delta K$=kd×K) for reducing the solid density differences $\Delta Ds$ to zero.

Then, at step S80, the online controlling section 16 corrects the key opening difference amounts $\Delta Kk$, $\Delta Kc$, $\Delta Km$, $\Delta Ky$ arithmetically operated by the color conversion section 14 taking the dead times from the printing units 2a, 2b, 2c and 2d to the line sensor type IRGB densitometer 1, reaction times of the ink keys 7 per unit time and the printing speed into consideration. In the correction, a time delay after a key opening signal is inputted until a corresponding ink key 7 moves to change the key opening thereby to change the ink amount to be supplied to the printing sheet and the variation of the ink amount appears as a variation of the reflected light amount on the line sensor type IRGB densitometer 1 is taken into consideration. For such an online feedback control system which involves considerable dead time as described above, for example, PI control with dead time compensation, fuzzy control or robust control is optically applied. The online controlling section 16 adds the key openings Kk0, Kc0, Km0, Ky0 at present to the key opening difference amounts (online control key opening differences) $\Delta Kk$, $\Delta Kc$, $\Delta Km$, $\Delta Ky$ to determine online control key openings Kk1, Kc1, Km1, Ky1 and inputs the determined online control key openings Kk1, Kc1, Km1, Ky1 to the key opening limiter arithmetic operation section 17.

At step S90, the key opening limiter arithmetic operation section 17 performs correction of restricting upper limit values to the online control key openings Kk1, Kc1, Km1, Ky1 arithmetically operated by the online controlling section 16. This is a process for restricting the key openings from increasing abnormally particularly arising from an estimated error of the color conversion algorithm (processes at steps S40, S50 and S60) in a low image area ratio region. Then at step S90, the key opening limiter arithmetic operation section 17 transmits the key openings Kk, Kc, Km, Ky whose upper limit values are restricted as key opening signals to the controlling apparatus 20 of the printing press.

At step S110, the controlling apparatus 20 adjusts the ink keys 7 of the printing units 2a, 2b, 2c and 2d based on the key openings Kk, Kc, Km, Ky received from the arithmetic operation apparatus 10. Consequently, the ink supplying amounts of the ink colors are controlled so as to conform to a target color tone for each key zone.

In this manner, with the color tone controlling method according to the present embodiment, the color tone control can be carried out immediately after build up of the printing press as described hereinabove. Then, noticed pixel regions (noticed points) are individually set and the color mixture halftone density of the noticed points is set as the target color mixture halftone densities Io, Ro, Go, Bo, and the actual color mixture halftone densities I, R, G, B of the corresponding noticed points on a main printing sheet are measured and used for feedback control. Consequently, also where plate making data such as 1 bit-Tiff or CIP4 data are not available, the color tone control can be performed for the specific noticed points of the picture.

Further, since measured values are not averaged over the entire key zone, even if the line ratio of the picture in the key zone is low (for example, even if the key zone includes a one-point small picture therein), the measurement error of the line sensor type IRGB densitometer 1 is small and the color tone control can be performed stably. Particularly, if a pixel having the highest density sensitivity is arithmetically operated and automatically extracted for each ink color and set as a noticed pixel region, then the color tone control can be performed more stably where the line ratio of the picture in the key zone is low. In particular, for example, the density sensitivity Hdc of cyan can be represented by "Hdc=$R^p$/(R+G+B+I)" using the measured density data (R, G, B, I), and the pixel having the highest value of the density sensitivity Hdc is determined as the noticed point of cyan (for example, approximately 1.3 is selected as the exponentiation p of the autocorrelation). Similarly, also with regard to the other ink colors, a pixel having the highest density sensitivity is arithmetically operated and the arithmetically operated pixel is set as the noticed point.

Particularly, in the case of the publicly known expansion Neugebauer expression (A) wherein the Yule-Nielsen coefficient n is set to such a value that the relationship between the tone values and the color mixture halftone density value becomes substantially linear, the relationship between the tone values and the color mixture halftone density becomes such a linear relationship as indicated by a solid line in FIG. 5. Therefore, also in a case wherein the density (density at present) of the actual printed matter comes out of the region within the color space (solid line circle) with respect to the standard density as indicated by a black round mark in FIG. 4, the relationship between the tone values and the color mixture halftone density in the color space region estimated with respect to the standard density can be easily extended and used. Also when an operator prints with a density higher than an estimated maximum density in accordance with a demand of a customer or the like, conversion from a color mixture halftone density into tone values can be performed with certainty, and actual tone values can be determined to carry out color tone control.

(B) Second Embodiment

A second embodiment of the present invention is described. In the present embodiment, the publicly known Neugebauer expression (B) which is dot gain corrected is used in place of the conversion table in the embodiment described above.

In particular, in place of the conversion table in the first embodiment produced based on the corresponding relationship obtained in advance by printing the color scale of the Japan Color (ISO12642) or the like under the standard density, the solid density values Di($\lambda$) of the wavelengths $\lambda$ of the colors of the colors of I (Infrared radiation), R (Red), G (Green), B (Blue) are acquired from data obtained in advance by printing the color scale of the Japan Color (ISO12642) or the like under the standard density and for which dot gain correction is performed, and the publicly known Neugebauer expression (B) for which dot gain correction is defined in such a manner as given below and the expression (B) is used to determine the color mixture halftone density.

[Expression 6]

$$10^{-Dao(\lambda)} = (1-k)(1-c)(1-m)(1-y) + k(1-c)(1-m)(1-y)10^{-Dk(\lambda)} + c(1-k)(1-m)(1-y)10^{-Dc(\lambda)} + m(1-k)(1-c)(1-y)10^{-Dm(\lambda)} + y(1-k)(1-c)(1-m)10^{-Dy(\lambda)} + kc(1-m)(1-y)10^{-Dkc(\lambda)} + km(1-c)(1-y)10^{-Dkm(\lambda)} + ky(1-k)(1-y)10^{-Dky(\lambda)} + cm(1-k)(1-y)10^{-Dcm(\lambda)} + cy(1-k)(1-m)10^{-Dcy(\lambda)} + my(1-k)(1-c)10^{-Dmy(\lambda)} + kcm(1-y)10^{-Dkcm(\lambda)} + kcy(1-m)10^{-Dkcy(\lambda)} + kmy(1-c)10^{-Dkmy(\lambda)} + cmy(1-k)10^{-Dcmy(\lambda)} + kcmy \cdot 10^{-Dkcmy(\lambda)}$$

(B)

where
Dao($\lambda$): target color mixture halftone density value,
k, c, m, y: tone values data in a dot gain corrected state,
Di($\lambda$): solid density value of wavelength $\lambda$ of each color i (extracted from color scale data),
i: one of Cyan, Magenta, Yellow, Black and color mixture of them,
for example, Dc: solid density value of Cyan, Dm: solid density value of Magenta,
Dy: solid density value of Yellow, Dk: solid density value of Black,
Dcm: two-color overlapping solid density value of Cyan and Magenta,
Dcy: two-color overlapping solid density value of Cyan and Yellow,
Dmy: two-color overlapping solid density value of Magenta and Yellow,
Dkc: two-color overlapping solid density value of Cyan and Black,
Dkm: two-color overlapping solid density value of Magenta and Black,
Dky: two-color overlapping solid density value of Yellow and Black,
Dcmy: three-color overlapping solid density value of Cyan, Magenta and Yellow,
Dkcm: three-color overlapping solid density value of Cyan, Magenta and Black,
Dkcy: three-color overlapping solid density value of Cyan, Yellow and Black,
Dkmy: three-color overlapping solid density value of Magenta, Yellow and Black,
Dcmyk: four-color overlapping solid density value of Cyan, Magenta, Yellow and Black, and
$\lambda$: wavelength region of each of R, G, B, I, for example, R=650 nm, G=550 nm, B=450 nm, and I=800 nm.

It is to be noted that, in the expression above, the Nielsen coefficient n in the publicly known expanded Neugebauer expression (A) described above is removed.

Also by this configuration, effects similar to those in the first embodiment can be achieved.

It is to be noted that, as regards the dot gain correction of the publicly known Neugebauer expression (B), the tone values data k, c, m, y in the expression (B) are dot gain corrected in the following manner.

First, monochromatic halftone densities Dc50 to Dk50 when the tone values of the plate making data are 50% and monochromatic solid densities (monochromatic solid halftone densities) Dc100 to Dk100 when the tone values of the plate making data are solid (100%) are obtained by extraction from the color scale density value data. Then, color dot gain amounts (values before correction) DGc' to DGk' when the monochromatic tone values of the plate making data are 50% are calculated using the following expression (C) based on the values obtained as above.

$$DGc'=(1-10^{-Dc50})/(1-10^{-Dc100})-0.5$$

$$DGm'=(1-10^{-Dm50})/(1-10^{-Dm100})-0.5$$

$$DGy'=(1-10^{-Dy50})/(1-10^{-Dy100})-0.5$$

$$DGk'=(1-10^{-Dk50})/(1-10^{-Dk100})-0.5 \quad (C)$$

where

DGc to DGk: color dot gain amount when the monochromatic tone values of the plate making data are 50%;

Dc50 to Dk50: monochromatic halftone density when the tone values of the plate making data are 50% (extracted from the color scale density value data); and Dc100 to Dk100: monochromatic solid density when the tone values of the plate making data are solid (100%) (extracted from the color scale density value data).

Then, using the following expression (D), correction is performed with dot gain correction coefficients kc, km, ky, kk to calculate color dot gain amounts (values after correction) DGc to DGk when the monochromatic tone values of the plate making data are 50%.

$$DGc=kc \times DGc'$$

$$DGm=km \times DGm'$$

$$DGy=ky \times DGy'$$

$$DGk=kk \times DGk' \quad (D)$$

where kc, km, ky, kk are the dot gain correction coefficients and normally are 1.

Then, by dot gain correcting plate making tone values data c' to k' using the following expression (E), corrected tone values data k, c, m, y can be obtained.

$$c=-DGc/0.25 \times (C'-0.5)^2+DGc+c'$$

$$m=-DGm/0.25 \times (m'-0.5)^2+DGm+m'$$

$$y=-DGy/0.25 \times (y'-0.5)^2+DGy+y'$$

$$k=-DGk/0.25 \times (k'-0.5)^2+DGk+k' \quad (E)$$

where c to k: tone values data for which dot gain correction is performed; and c' to k': plate making tone values data.

By changing such a dot gain correction coefficient as described above, the target density can be changed. For example, where the dot gain increases because of degradation of a blanket or the like of the printing press, if the dot gain correction coefficient is increased from 1, then the target value can be calculated with accuracy.

(C) Third Embodiment

Figure 8:
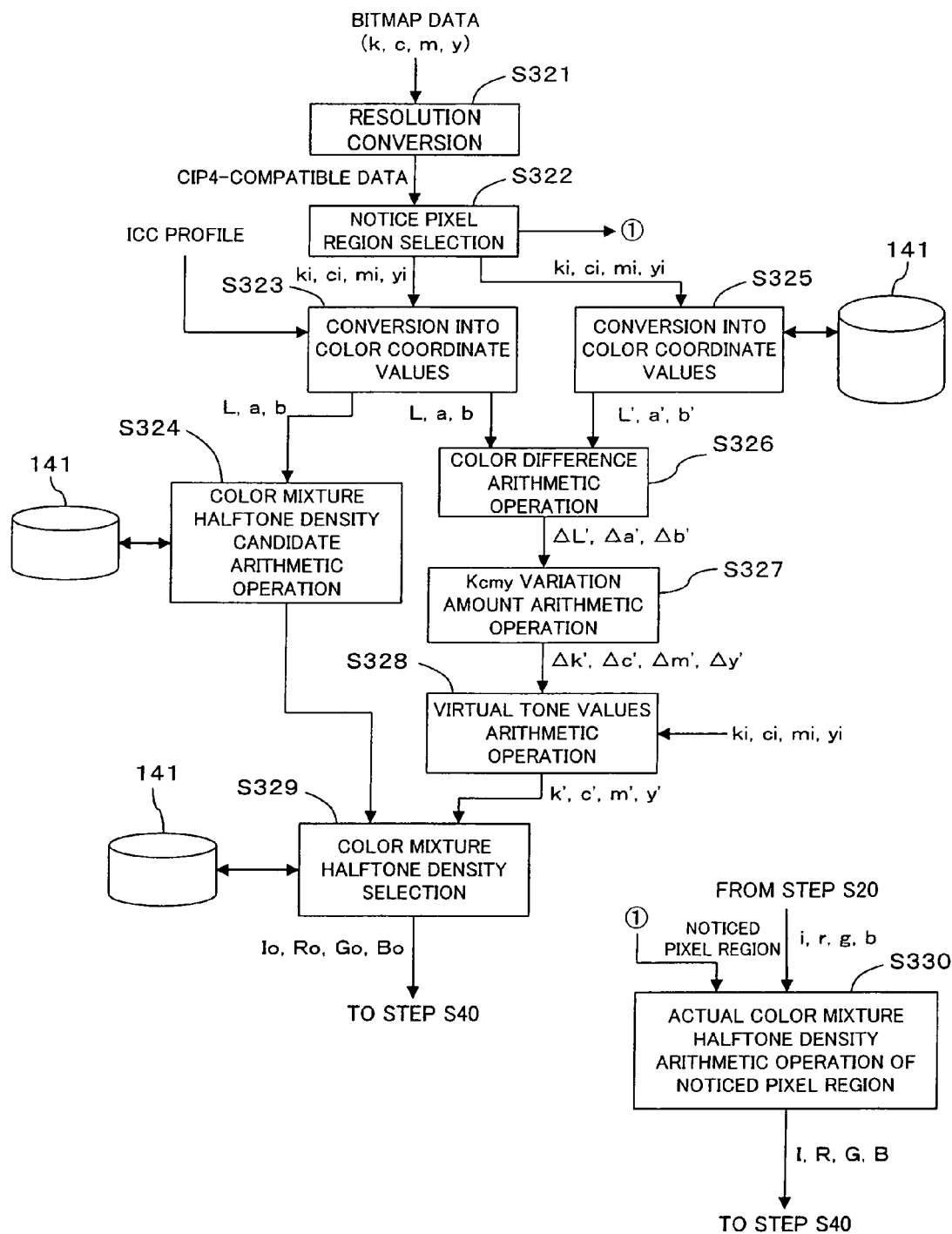
FIG. 8 is a flow chart illustrating a processing flow of color tone control according to a third embodiment of the present invention.
Figure 9:
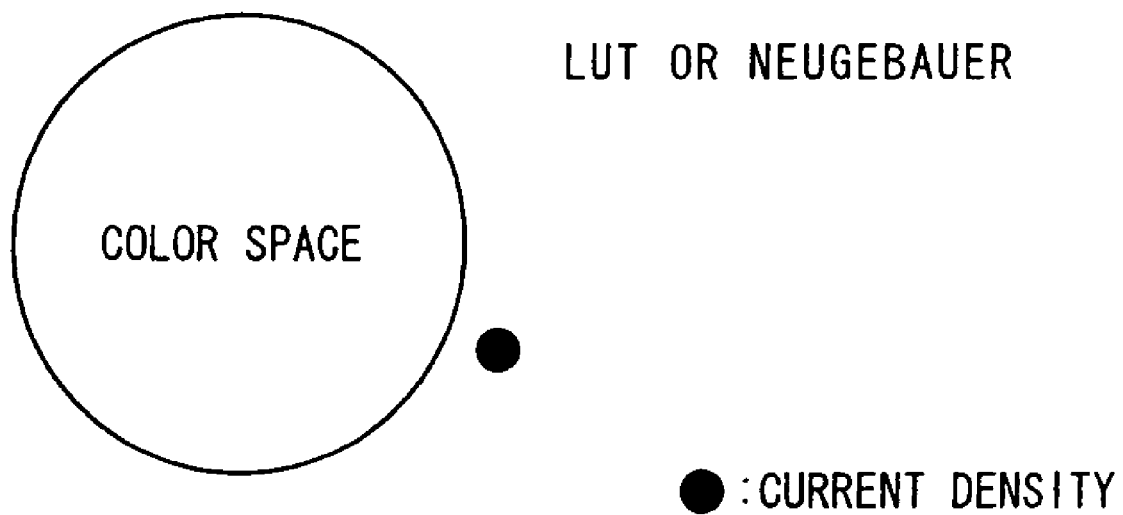
FIG. 9 is a view illustrating a subject to be solved by the present invention.

A third embodiment of the present invention is described with reference to FIG. 8. The present embodiment is characterized in the setting method of the target density (target color mixture halftone density) of a noticed pixel region (noticed point). A flow chart shown in FIG. 8 illustrates the substance of processing (substance of a process corresponding to that at step S04 in FIG. 3) in the present embodiment in detail. Since the substance of the other processes for picture color tone control is such as described hereinabove with reference to FIG. 3, description of the substance is omitted here.

It is assumed that, also in the present embodiment, printing data of page information for a newspaper transmitted in the form of bitmap data from a base station of a newspaper company to a printing factory are inputted similarly as in the first embodiment. However, in the present embodiment, as a difference from the second embodiment, also an ICC profile of an inputting apparatus by which color information of the page has been produced is transmitted in addition to the bitmap data of the page information. At step S321, the bitmap data are converted into low-resolution data corresponding to CIP4 data according to the format of the printing press, and at step S322, a noticed point corresponding to each ink color is set for each ink supplying unit width. Since the substance of the processes at steps S321 and S322 is similar to that at steps S311 and S312 according to the second embodiment, detailed description thereof is omitted.

At step S323, the ICC profile received from the base station of the newspaper company is used to convert the tone values ki, ci, mi, yi of the noticed points into a color coordinate value L, a, b. Then at step S324, a conversion table stored in the database 141 is used to convert the color coordinate value L, a, b determined at step S324 into a color mixture halftone density. However, since the color mixture halftone density is four-dimensional information while the color coordinate value is three-dimensional information, the color mixture halftone density corresponding to the color coordinate value is not determined uniquely. In order to determine the color mixture halftone density uniquely, some additional information is required. However, from the ICC profile, only three-dimensional information of the color coordinate value can be obtained.

Therefore, in the present embodiment, the tone values data of the printing picture, that is, the tone values ki, ci, mi, yi corresponding to the color coordinate value L, a, b, are utilized to select, in development from such three-dimensional information into four-dimensional information, the most appropriate pieces of four-dimensional information from among a large number of pieces of the four-dimensional information which are regarded as candidates.

First at step S325, the conversion table stored in the database 141 is used to convert the tone values ki, ci, mi, yi of the noticed points into color coordinate values L', a', b'. At step S326, color differences $\Delta L'$, $\Delta a'$, $\Delta b'$ between the color coordinate values L, a, b determined at step S323 and the color coordinate values L', a', b' determined at step S325 are arithmetically operated. Then at step S327, variation amounts $\Delta k'$, $\Delta c'$, $\Delta m'$, $\Delta y'$ of the tone values corresponding to the color differences $\Delta L'$, $\Delta a'$, $\Delta b'$, respectively, are arithmetically operated. The variation amounts of the tone values can be approximated by the following expressions using the variation amounts of the color coordinate values. It is to be noted that a and b in the following expressions are linear approximation coefficients.

$$\Delta c'=a11 \times \Delta L'+a12 \times \Delta a'+a13 \times \Delta b'+bc \quad (1)$$

$$\Delta m'=a21 \times \Delta L'+a22 \times \Delta a'+a23 \times \Delta b'+bm \quad (2)$$

$$\Delta y'=a31 \times \Delta L'+a32 \times \Delta a'+a33 \times \Delta b'+by \quad (3)$$

$$\Delta k'=a41 \times \Delta L'+a42 \times \Delta a'+a43 \times \Delta b'+bk \quad (4)$$

At step S328, the variation amounts $\Delta k'$, $\Delta c'$, $\Delta m'$, $\Delta y'$ determined at step S327 are added to the tone values ki, ci, mi, yi of the noticed points, and the resulting values are set as virtual tone values k', c', m', y', respectively. At step S329, the virtual tone values k', c', m', y' are applied to the conversion table recorded in the database 141 to select, from among the color mixture halftone density candidates determined at step S324, those which correspond most to the virtual tone values k', c', m', y'. The selected color mixture halftone densities are set as the target color mixture halftone densities Io, Ro, Go, Bo and are used in the processes at steps beginning with step S40 together with the actual color mixture halftone densities I, R, G, B of the noticed points arithmetically operated at step S330.

According to the present method, since an ICC profile obtained from a printing requesting source or the like can be used to control the color tone, the color tone can be adjusted accurately and easily to a color tone desired by the printing requesting source or the like when compared with alternative color adjustment which is performed through comparison with a proof-sheet as is performed conventionally. Accordingly, with the present method, the appearing amount of paper loss before an OK sheet is obtained can be reduced significantly.

While the embodiments of the present invention are described above, the embodiments of the present invention are not limited to those described above. For example, while the line sensor type IRGB densitometer is used in the embodiments described above, a spot type IRGB densitometer may be used to scan a printing sheet two-dimensionally.

INDUSTRIAL APPLICABILITY OF THE INVENTION

According to the present invention, also when printing is performed with a density exceeding an estimated maximum density (reference density), it is possible to expand the color space and use an IRGB densitometer to perform color tone control, and it is possible to cope with various demands for the printing color tone. Further, since an IRGB densitometer is used, the present invention can be applied also to picture color tone control in such high speed printing as in the case of, for example, a rotary press for newspapers and can be applied to various printing application.

The invention claimed is:

1. A picture color tone controlling method for a printing press, comprising:

a noticed pixel region selection step of selecting a noticed pixel region to be noticed as an object of picture color tone control in a printing picture;

a target color mixture halftone density setting step of setting a target color mixture halftone density regarding the noticed pixel region selected at the noticed pixel region selection step;

an actual color mixture halftone density measurement step of measuring an actual color mixture halftone density for each noticed pixel region on an actually printed sheet obtained by printing using an IRGB densitometer;

a target tone values calculation step of calculating target tone values of each ink color corresponding to the target color mixture halftone density based on a corresponding relationship between tone values and color mixture halftone densities set in advance;

an actual tone values calculation step of calculating actual tone values for each ink color corresponding to the actual color mixture halftone density based on the corresponding relationship between the tone values and the color mixture halftone densities;

a target monochromatic halftone density calculation step of calculating a target monochromatic halftone density corresponding to the target tone values based on a corresponding relationship between tone values and monochromatic halftone densities set in advance;

an actual monochromatic halftone density calculation step of calculating an actual monochromatic halftone density corresponding to the actual tone values based on the corresponding relationship between the tone values and the monochromatic halftone densities;

a solid density difference calculation step of calculating a solid density difference corresponding to a difference between the target monochromatic halftone density and the actual monochromatic halftone density under the target tone values based on a corresponding relationship among tone values, monochromatic halftone densities and solid densities set in advance; and an ink supplying amount adjustment step of adjusting an ink supplying amount for each ink supplying unit width of an ink supplying apparatus based on the solid density difference; and wherein, at the target tone values calculation step and the actual tone values calculation step, as the corresponding relationship between the tone values and the color mixture halftone densities, solid density values $Di(\lambda)$ for wavelengths $\lambda$ of colors of I (infrared light), R (Red), G (Green), and B (Blue) are acquired in advance and a publicly known extended Neugebauer expression (A) is produced in advance wherein a Yule-Nielsen coefficient n is set to such a value that the tone values and the color mixture halftone density value have a substantially linear relationship to each other, and the target tone values and the actual tone values are determined using the publicly known extended Neugebauer expression (A):

[Expression 1]

$$10^{-Da(\lambda)/n} = (1-K)(1-c)(1-m)(1-y) + k(1-c)(1-m)(1-y)$$
$$10^{-Dk(\lambda)/n} + c(1-k)(1-m)(1-y)10^{-Dc(\lambda)/n} + m(1-k)$$
$$(1-c)(1-y)10^{-Dm(\lambda)/n} + y(1-k)(1-c)(1-m)$$
$$10^{-Dy(\lambda)/n} + kc(1-m)(1-y)10^{-Dkc(\lambda)/n} + km(1-c)(1-y)10^{-Dkm(\lambda)/n} + ky(1-c)(1-m)10^{-Dky(\lambda)/n} + cm(1-k)$$
$$(1-y)10^{-Dcm(\lambda)/n} + cy(1-k)(1-m)10^{-Dcy(\lambda)/n} + my$$
$$(1-k)(1-c)10^{-Dmy(\lambda)/n} + kcm(1-y)10^{-Dkcm(\lambda)/n} + kcy$$
$$(1-m)10^{-Dkcy(\lambda)/n} + kmy(1-c)10^{-Dkmy(\lambda)/n} + cmy(1-k)10^{-Dcmy(\lambda)/n} + kcmy10^{-Dkcmy(\lambda)/n} \quad (A)$$

where $Da(\lambda)$: color mixture halftone density value;

k, c, m, y: tone values of corresponding inks;

$Di(\lambda)$: solid density value of wavelength $\lambda$ of each color i (extracted from color scale data);

i: one of Cyan, Magenta, Yellow, Black and color mixture of them;

for example, Dc: solid density value of Cyan, Dm: solid density value of Magenta;

Dy: solid density value of Yellow; Dk: solid density value of Black;

Dcm: two-color overlapping solid density value of Cyan and Magenta;

Dcy: two-color overlapping solid density value of Cyan and Yellow;

Dmy: two-color overlapping solid density value of Magenta and Yellow;

Dkc: two-color overlapping solid density value of Cyan and Black;

Dkm: two-color overlapping solid density value of Magenta and Black

Dky: two-color overlapping solid density value of Yellow and Black;

Dcmy: three-color overlapping solid density value of Cyan, Magenta and Yellow;

Dkcm: three-color overlapping solid density value of Cyan, Magenta and Black;

Dkcy: three-color overlapping solid density value of Cyan, Yellow and Black;

Dkmy: three-color overlapping solid density value of Magenta, Yellow and Black;

Dcmyk: four-color overlapping solid density value of Cyan, Magenta, Yellow and Black $\lambda$: wavelength region of each of R, G, B, I, for example, R =650 nm, G =550 nm, B=450 nm, I=800 nm; and n: coefficient of Yule-Nielsen.

2. The picture color tone controlling method for a printing press as set forth in claim 1, wherein the solid density value $Di(\lambda)$ for each of the wavelengths $\lambda$ of the colors of I (infrared light), R (Red), G (Green) and B (Blue) in the publicly known extended Neugebauer expression (A) is acquired from data obtained in advance by printing a color scale of the Japan Color (ISO12642) or the like under the standard density.

3. The picture color tone controlling method for a printing press as set forth in claim 1, wherein the target color mixture halftone density setting step includes a data acquisition step of acquiring tone values data of kcmy of a printing object picture from the outside, and a color mixture halftone density conversion step of converting the tone values of the noticed pixel regions acquired at the data acquisition step into color mixture halftone densities based on the corresponding relationship between the tone values and the color mixture halftone densities set in advance, the color mixture halftone densities of the noticed pixel regions converted at the color mixture halftone density conversion step being set as the target color mixture halftone densities.

4. The picture color tone controlling method for a printing press as set forth in claim 3, wherein the corresponding relationship between the tone values and the color mixture halftone densities used at the color mixture halftone density conversion step is defined as a conversion table produced based on a corresponding relationship obtained in advance by printing a color scale of the Japan Color (ISO12642) or the like under the standard density or the publicly known Neugebauer expression (B) wherein solid density values $Di(\lambda)$ of the wavelengths $\lambda$ of the colors of I (infrared light), R (Red), G (Green), and B (Blue) are obtained in advance by printing a color scale of the Japan Color (ISO12642) or the like under the standard density and then dot gain corrected, and a color mixture halftone density is determined using the conversion table or the publicly known Neugebauer expression (B) in the dot gain corrected state:

[Expression 2]

$$10^{-Dao(\lambda)} = (1-k)(1-c)(1-m)(1-y) + k(1-c)(1-m)(1-y)10^{-Dk(\lambda)} + c(1-k)(1-m)(1-y)10^{-Dc(\lambda)} + m(1-k)(1-c)(1-y)10^{-Dm(\lambda)} + y(1-k)(1-c)(1-m)10^{-Dy(\lambda)} + kc(1-m)(1-y)10^{-Dkc(\lambda)} + km(1-c)(1-y)10^{-Dkm(\lambda)} + ky(1-c)(1-m)10^{-Dky(\lambda)} + cm(1-k)(1-y)10^{-Dcm(\lambda)} + cy(1-k)(1-m)10^{-Dcy(\lambda)} + my(1-k)(1-c)10^{-Dmy(\lambda)} + kcm(1-y)10^{-Dkcm(\lambda)} + kcy(1-m)10^{-Dkcy(\lambda)} + kmy(1-c)10^{-Dkmy(\lambda)} + cmy(1-k)10^{-Dcmy(\lambda)} + kcmy \cdot 10^{-Dkcmy(\lambda)}$$

(B)

where $Dao(\lambda)$: target color mixture halftone density value;

k, c, m, y: tone values data in a dot gain corrected state;

$Di(\lambda)$: solid density value of wavelength $\lambda$ of each color i (extracted from color scale data);

i: one of Cyan, Magenta, Yellow, Black and color mixture of them;

for example, Dc: solid density value of Cyan, Dm: solid density value of Magenta, Dy: solid density value of Yellow, Dk: solid density value of Black;

Dcm: two-color overlapping solid density value of Cyan and Magenta;

Dcy: two-color overlapping solid density value of Cyan and Yellow;

Dmy: two-color overlapping solid density value of Magenta and Yellow;

Dkc: two-color overlapping solid density value of Cyan and Black;

Dkm: two-color overlapping solid density value of Magenta and Black;

Dky: two-color overlapping solid density value of Yellow and Black;

Dcmy: three-color overlapping solid density value of Cyan, Magenta and Yellow;

Dkcm: three-color overlapping solid density value of Cyan, Magenta and Black;

Dkcy: three-color overlapping solid density value of Cyan, Yellow and Black;

Dkmy: three-color overlapping solid density value of Magenta, Yellow and Black;

Dcmyk: four-color overlapping solid density value of Cyan, Magenta, Yellow and Black; and $\lambda$: wavelength region of each of R, G, B, I, for example, R =650 nm, G =550 nm, B =450 nm, and I =800 nm.

5. The picture color tone controlling method for a printing press as set forth in claim 1, wherein the target color mixture halftone density setting step includes:

a data acquisition step of acquiring kcmy tone values data and an ICC profile of a printing object picture from the outside; and a color mixture halftone density conversion step of converting the tone values of the noticed pixel region into a color mixture halftone density using the ICC profile and a device profile of the IRGB densitometer;

the color mixture halftone density of the noticed pixel region converted at the color mixture halftone density conversion step being set as the target color mixture halftone density.

6. The picture color tone controlling method for a printing press as set forth in claim 5, wherein the device profile is a conversion table which defines a corresponding relationship among tone values, color mixture halftone densities and color coordinate values, and the color mixture halftone density conversion step includes:

a first color coordinate value conversion step of converting the tone values of the noticed pixel into a color coordinate value using the ICC profile;

a color mixture halftone density candidate selection step of selecting a plurality of color mixture halftone density candidates corresponding to the color coordinate value of the noticed pixel using the conversion table;

a second color coordinate value conversion step of converting the tone values of the noticed pixel into another color coordinate value using the conversion table;

a color difference calculation step of calculating a color difference between the two color coordinate values obtained at the first and second color coordinate value conversion steps;

a tone values variation amount calculation step of calculating a variation amount of the tone values corresponding to the color difference calculated at the color difference calculation step;

a virtual tone values calculation step of calculating virtual tone values by adding the variation amount calculated at the tone values variation amount calculation step to the tone values of the noticed pixel region; and a selection step of referring to the conversion table to select a color mixture halftone density candidate which most corresponds to the virtual tone values calculated at the virtual tone values calculation step from among the plural color mixture halftone density candidates selected at the color mixture halftone density candidate selection step;

the selected color mixture halftone density candidate being set as the color mixture halftone density of the noticed pixel region at the color mixture halftone density conversion step.

7. The picture color tone controlling method for a printing press as set forth in claim 5, wherein, at the data acquisition step, bitmap data of the printing object picture are acquired first, and then, data produced by converting the bitmap data into low-resolution data corresponding to CIP4 data is used as the kcmy halftone dot area data.

8. The printing color tone controlling method for a printing press as set forth in claim 1, wherein, at the noticed pixel region selection step, a region in which the autocorrelation is high regarding each ink color is selected in a unit of a sensor pixel of the IRGB densitometer, and the selected region is set as the noticed pixel region for each ink color.

9. The Picture color tone controlling method for a printing press as set forth in claim 8, wherein the region in which the autocorrelation is high at the noticed pixel region selection step is all pixel groups whose autocorrelation is higher than a condition set in advance for each ink color, and, at the noticed pixel setting step, the pixel group is automatically extracted using a computer.

10. A picture color tone controlling apparatus for a printing press, comprising:

an ink supplying apparatus for supplying ink to individual regions divided in a printing widthwise direction;

noticed pixel region selection means for selecting a noticed pixel region to be noticed as an object of color tone control in a printing picture;

target color mixture halftone density setting means for setting a target color mixture halftone density regarding the noticed pixel region selected by the noticed pixel region selection step;

an IRGB densitometer disposed on a traveling line of an actually printed sheet obtained by printing;

color mixture halftone density measurement means for operating said IRGB densitometer to measure an actual color mixture halftone density for each noticed pixel region of the actually printed sheet;

target tone values calculation means for determining target tone values for each ink color corresponding to the target color mixture halftone density based on a corresponding relationship between tone values and color mixture halftone densities set in advance;

actual tone values calculation means for calculating actual tone values for each ink color corresponding to the actual color mixture halftone density based on the corresponding relationship between the tone values and the color mixture halftone densities;

target monochromatic halftone density calculation means for calculating a target monochromatic halftone density corresponding to the target tone values based on a corresponding relationship between tone values and monochromatic halftone densities set in advance;

actual monochromatic halftone density calculation means for calculating an actual monochromatic halftone density corresponding to the actual tone values based on the corresponding relationship between the tone values and the monochromatic halftone densities;

solid density difference calculation means for calculating a solid density difference corresponding to a difference between the target monochromatic halftone density and the actual monochromatic halftone density under the target tone values based on a corresponding relationship among tone values, monochromatic halftone densities and solid densities set in advance; and ink supplying amount adjustment means for adjusting an ink supplying amount for each ink supplying unit width based on the solid density difference;

said target tone values calculation means and said actual tone values calculation means being operable to acquire, as the corresponding relationship between tone values and color mixture halftone densities, solid density values $Di(\lambda)$ for wavelengths $\lambda$ of colors of I (Infrared light), R (Red), G (Green), and B (Blue) in advance, produce the publicly known extended Neugebauer expression (A) in advance wherein a Yule-Nielsen coefficient n is set to such a value that the tone values and the color mixture halftone density have a substantially linear relationship to each other, and determine the target tone values and the actual tone values using the publicly known extended Neugebauer expression (A):

[Expression 3]

$$10^{-Dao(\lambda)/n} = (1-K)(1-c)(1-m)(1-y) + k(1-c)(1-m)(1-y)10^{-Dk(\lambda)/n} + c(1-k)(1-m)(1-y)10^{-Dc(\lambda)/n} + m(1-k)(1-c)(1-y)10^{-Dm(\lambda)/n} + y(1-k)(1-c)(1-m)10^{-Dy(\lambda)/n} + kc(1-m)(1-y)10^{-Dkc(\lambda)/n} + km(1-c)(1-y)10^{-Dkm(\lambda)/n} + ky(1-c)(1-m)10^{-Dky(\lambda)/n} + cm(1-k)(1-y)10^{-Dcm(\lambda)/n} + cy(1-k)(1-m)10^{-Dcy(\lambda)/n} + my(1-k)(1-c)10^{-Dmy(\lambda)/n} + kcm(1-y)10^{-Dkcm(\lambda)/n} + kcy(1-m)10^{-Dkcy(\lambda)/n} + kmy(1-c)10^{-Dkmy(\lambda)/n} + cmy(1-k)10^{-Dcmy(\lambda)/n} + kcmy10^{-Dkcmy(\lambda)/n} \quad (A)$$

where $Da(\lambda)$: color mixture halftone density value;

k, c, m, y: tone values of corresponding inks;

$Di(\lambda)$: solid density value of wavelength $\lambda$ of each color i (extracted from color scale data);

i: one of Cyan, Magenta, Yellow, Black and color mixture of them;

for example, Dc: solid density value of Cyan, Dm: solid density value of Magenta, Dy: solid density value of Yellow, Dk: solid density value of Black;

Dcm: two-color overlapping solid density value of Cyan and Magenta

Dcy: two-color overlapping solid density value of Cyan and Yellow

Dmy: two-color overlapping solid density value of Magenta and Yellow;

Dkc: two-color overlapping solid density value of Cyan and Black;

Dkm: two-color overlapping solid density value of Magenta and Black;

Dky: two-color overlapping solid density value of Yellow and Black;

Dcmy: three-color overlapping solid density value of Cyan, Magenta and Yellow;

Dkcm: three-color overlapping solid density value of Cyan, Magenta and Black;

Dkcy: three-color overlapping solid density value of Cyan, Yellow and Black;

Dkmy: three-color overlapping solid density value of Magenta, Yellow and Black;

Dcmyk: four-color overlapping solid density value of Cyan, Magenta, Yellow and Black λ: wavelength region of each of R, G, B, I, for example, R =650 nm, G =550 nm, B=450 nm, I=800 nm; and n: coefficient of Yule-Nielsen.

11. The picture color tone controlling apparatus for a printing press as set forth in claim 10, wherein the solid density value Di(λ) for each of the wavelengths λ of the colors of I (infrared light), R (Red), G (Green) and B (Blue) in the publicly known extended Neugebauer expression (A) is acquired from data obtained in advance by printing a color scale of the Japan Color (ISO12642) or the like under the standard density.

12. The picture color tone controlling apparatus for a printing press as set forth in claim 10, wherein said target color mixture halftone density setting means includes:

data acquisition means for acquiring tone values data of kcmy of a printing object picture from the outside; and color mixture halftone density conversion means for converting the tone values of the noticed pixel region acquired by said data acquisition means into color mixture halftone density based on the corresponding relationship between the tone values and the color mixture halftone densities set in advance;

the color mixture halftone density of the noticed pixel region converted by said color mixture halftone density conversion means being set as the target color mixture halftone density.

13. The picture color tone controlling apparatus for a printing press as set forth in claim 12, wherein the corresponding relationship between the tone values and the color mixture halftone densities used by said color mixture halftone density conversion means is defined as a conversion table produced based on a corresponding relationship obtained in advance by printing a color scale of Japan Color (ISO12642) or the like under the standard density or the publicly known Neugebauer expression (B) wherein solid density values Di(λ) of the wavelengths λ of the colors of I (infrared light), R (Red), G (Green), and B (Blue) are obtained in advance by printing a color scale of the Japan Color (ISO12642) or the like under the standard density and then dot gain corrected, and a color mixture halftone density is determined using the conversion table or the publicly known Neugebauer expression (B) in the dot gain corrected state:

[Expression 4]

$$10^{-Dao(\lambda)} = (1-k)(1-c)(1-m)(1-y) + k(1-c)(1-m)(1-y)10^{-Dk(\lambda)} + c(1-k)(1-m)(1-y)10^{-Dc(\lambda)} + m(1-k)(1-c)(1-y)10^{-Dm(\lambda)} + y(1-k)(1-c)(1-m)10^{-Dy(\lambda)} + kc(1-m)(1-y)10^{-Dkc(\lambda)} + km(1-c)(1-y)10^{-Dkm(\lambda)} + ky(1-k)(1-y)10^{-Dky(\lambda)} + cm(1-k)(1-y)10^{-Dcm(\lambda)} + cy(1-k)(1-m)10^{-Dcy(\lambda)} + my(1-k)(1-c)10^{-Dmy(\lambda)} + kcm(1-y)10^{-Dkcm(\lambda)} + kcy(1-m)10^{-Dkcy(\lambda)} + kmy(1-c)10^{-Dkmy(\lambda)} + cmy(1-k)10^{-Dcmy(\lambda)} + kcmy \cdot 10^{-Dkcmy(\lambda)} \quad (B)$$

where

Dao(λ): target color mixture halftone density value;

k, c, m, y: tone values data in a dot gain corrected state;

Di(λ): solid density value of wavelength λ, of each color i (extracted from color scale data);

i: one of Cyan, Magenta, Yellow, Black and color mixture of them;

for example, Dc: solid density value of Cyan, Dm: solid density value of Magenta;

Dy: solid density value of Yellow, Dk: solid density value of Black;

Dcm: two-color overlapping solid density value of Cyan and Magenta;

Dcy: two-color overlapping solid density value of Cyan and Yellow;

Dmy: two-color overlapping solid density value of Magenta and Yellow;

Dkc: two-color overlapping solid density value of Cyan and Black;

Dkm: two-color overlapping solid density value of Magenta and Black;

Dky: two-color overlapping solid density value of Yellow and Black;

Dcmy: three-color overlapping solid density value of Cyan, Magenta and Yellow;

Dkcm: three-color overlapping solid density value of Cyan, Magenta and Black;

Dkcy: three-color overlapping solid density value of Cyan, Yellow and Black;

Dkmy: three-color overlapping solid density value of Magenta, Yellow and Black;

Dcmyk: four-color overlapping solid density value of Cyan, Magenta, Yellow and Black; and λ: wavelength region of each of R, G, B, I, for example, R =650 nm, G =550 nm, B =450 nm, and I =800 nm.

14. The picture color tone controlling apparatus for a printing press as set forth in claim 10, further comprising noticed pixel region selection means (computer) for automatically extracting, as the noticed pixel region for each ink color, all pixel groups whose autocorrelation is higher than a condition set in advance for each ink color.

* * * * *